US011931197B2

(12) United States Patent
Li

(10) Patent No.: US 11,931,197 B2
(45) Date of Patent: Mar. 19, 2024

(54) SYSTEMS AND METHODS FOR CLOCK SYNCHRONIZATION

(71) Applicant: SHANGHAI UNITED IMAGING HEALTHCARE CO., LTD., Shanghai (CN)

(72) Inventor: Jun Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 184 days.

(21) Appl. No.: 17/456,557

(22) Filed: Nov. 24, 2021

(65) Prior Publication Data
US 2022/0079545 A1 Mar. 17, 2022

Related U.S. Application Data

(63) Continuation of application No. PCT/CN2020/093278, filed on May 29, 2020.

(30) Foreign Application Priority Data

May 29, 2019 (CN) .......................... 201910469299.8
Mar. 31, 2020 (CN) .......................... 202010244233.1

(51) Int. Cl.
*H04J 3/06* (2006.01)
*A61B 6/00* (2006.01)
(Continued)

(52) U.S. Cl.
CPC .............. *A61B 6/545* (2013.01); *A61B 6/037* (2013.01); *G01T 1/2985* (2013.01); *H03L 7/08* (2013.01)

(58) Field of Classification Search
None
See application file for complete search history.

(56) References Cited

U.S. PATENT DOCUMENTS 10,313,098 B2 * 6/2019 Cui ..................... A61B 6/582
11,483,007 B1 * 10/2022 Lam .................... H03M 1/0836
(Continued)

FOREIGN PATENT DOCUMENTS

CN 103488247 A 1/2014
CN 105262463 A 1/2016
(Continued)

OTHER PUBLICATIONS

International Search Report in PCT/CN2020/093278 dated Aug. 27, 2020, 4 pages.
(Continued)

*Primary Examiner* — Jeffery S Zweizig
(74) *Attorney, Agent, or Firm* — METIS IP LLC

(57) ABSTRACT

The present disclosure relates to systems and methods for clock synchronization. The system may include a reset signal generator connected with a plurality of detectors. The reset signal generator may be configured to generate a set of preliminary reset signals to be detected and transmit the set of preliminary reset signals to the plurality of detectors. Each of the set of preliminary reset signals may have a different phase. Each of the plurality of detectors may be configured to generate first feedback data for each of the set of preliminary reset signals and transmit the first feedback data to the reset signal generator. The reset signal generator may be further configured to generate, for each of the plurality of detectors, a reset signal based on the first feedback data and transmit the reset signal to each of the plurality of detectors. Each of the plurality detectors may be further configured to execute a clock synchronization in itself based on the reset signal.

19 Claims, 15 Drawing Sheets

(51) Int. Cl.
*A61B 6/03* (2006.01)
*G01T 1/29* (2006.01)
*H03L 7/08* (2006.01)

(56) References Cited

U.S. PATENT DOCUMENTS

| | | |
|---|---|---|
| 2004/0056202 A1 | 3/2004 | Rao |
| 2017/0302281 A1 | 10/2017 | Ning et al. |
| 2018/0123773 A1 | 5/2018 | Cui et al. |
| 2019/0268003 A1 | 8/2019 | Loinaz |

FOREIGN PATENT DOCUMENTS

| | | |
|---|---|---|
| CN | 105553594 A | 5/2016 |
| CN | 106667516 A | 5/2017 |
| CN | 107168458 A | 9/2017 |
| CN | 108324308 | 7/2018 |
| CN | 108494399 A | 9/2018 |
| CN | 108988858 A | 12/2018 |
| CN | 109150179 A | 1/2019 |
| CN | 110176975 A | 8/2019 |
| WO | 2013128363 A2 | 9/2013 |

OTHER PUBLICATIONS

Written Opinion in PCT/CN2020/093278 dated Aug. 27, 2020, 5 pages.

First Office Action in Chinese Application No. 201910469299.8 dated May 13, 2020, 14 pages.

Tu, Shenjun et al., Timing Sigal Benchmark Module Design for All-Digital PET System, Computer & Digital Engineering, 39(4): 182-185, 2011.

Ramón J. Aliaga et al., PET System Synchronization and Timing Resolution Using High-Speed Data Links, IEEE Transactions On Nuclear Science, 58(4): 1596-1605, 2011.

The Extended European Search Report in European Application No. 20813975.8 dated May 17, 2022, 9 pages.

\* cited by examiner

SYSTEMS AND METHODS FOR CLOCK SYNCHRONIZATION

CROSS-REFERENCE TO RELATED APPLICATIONS

This application is a Continuation of International Application No. PCT/CN2020/093278, filed on May 29, 2020, which claims priority to Chinese Patent Application No. 2019104692998 filed on May 29, 2019 and Chinese Patent Application No. 2020102442331 filed on Mar. 31, 2020, the contents of each of which are incorporated herein by reference in their entirety.

TECHNICAL FIELD

The present disclosure generally relates to medical imaging technology, and more particularly, relates to systems and methods for clock synchronization in a plurality of detectors.

BACKGROUND

Positron emission tomography (PET) is a nuclear imaging technology widely utilized in disease diagnosis and/or treatment for various medical conditions (e.g., tumors, coronary heart diseases, or brain disease) using radioactive materials. A radioactive tracer is injected into a patient's body and gets trapped within the tissues of interest. A PET system detects the radiation rays (e.g., y rays) emitted by the radioactive tracer for detecting or measuring changes in physiological activities in the tissues like metabolism, blood flow, regional chemical composition, and absorption, and therefore. The PET system may include a plurality of PET detectors. In order to obtain a clear and complete medical image of the patient, it is necessary to synchronize the detections of the plurality of PET detectors. Conventionally, this synchronization is done by transmitting a reset signal to the plurality of PET detectors for simultaneously starting the plurality of PET detectors' time counters or resetting them to zero, wherein the time counters are used to record a number of the occurrence of the detection of the radiation rays. However, due to, for example, differences in transmission and detection environments, one of the plurality of PET detectors may detect a jump edge of the reset signal, which may result in this PET detector's time counter starting or resetting different from other PET detectors', for example, one cycle difference. Therefore, it is desirable to provide new systems and methods for clock synchronization in the plurality of PET detectors, thereby improving the synchronization of the plurality of PET detectors.

SUMMARY

An aspect of the present disclosure relates to a system for clock synchronization. The system may include a reset signal generator connected with a plurality of detectors. The reset signal generator may be configured to generate a set of preliminary reset signals, each of which has a different phase, to be detected and transmit the set of preliminary reset signals to the plurality of detectors. Each of the plurality of detectors may be configured to generate first feedback data for each of the set of preliminary reset signals and transmit the first feedback data to the reset signal generator. The reset signal generator may be further configured to generate, for each of the plurality of detectors, a reset signal based on the first feedback data and transmit the reset signal to each of the plurality of detectors. Each of the plurality detectors may be further configured to execute a clock synchronization in itself based on the reset signal.

In some embodiments, to generate the first feedback data for each of the set of preliminary reset signals, each of the plurality of detectors may be further configured to, for each of the set of preliminary reset signals, correspondingly generate a sequence of sampling values based on a sequence of clock cycle iteration with different phases and take the sequence of sampling values as the first feedback data.

In some embodiments, to generate the reset signal based on the first feedback data, the reset signal generator may be further configured to determine an optimum phase of the reset signal and generate the reset signal with the optimum phase. A sampling value of a preliminary reset signal, of the plurality of the preliminary reset signal, with the optimum phase may be positive. The sampling value may be predicted based on the clock cycle iteration with a zero phase.

In some embodiments, to generate the reset signal based on the first feedback data, the reset signal generator may be further configured to determine an optimum preliminary reset signal, of which a first value of the sequence of sampling values is positive; and generate the reset signal with the phase of the optimum preliminary reset signal.

In some embodiments, each of the plurality of detectors may be further configured to generate second feedback data based on the reset signal and transmit the second feedback data to the reset signal generator. The reset signal generator may be further configured to determine whether the second feedback data corresponds to a predetermined value and transmit a determination instruction indicating that the reset signal has been correctly transmitted in response to determining that the second feedback value corresponds to the predetermined value.

A further aspect of the present disclosure relates to a method for clock synchronization. The method may include generating, by a reset signal generator connected with a plurality of detectors, a set of preliminary reset signals, each of which has a different phase, to be detected; transmitting the set of preliminary reset signals by the reset signal generator to the plurality of detectors; for each of the set of preliminary reset signals, generating first feedback data by each of the plurality of detectors; transmitting the first feedback data by each of the plurality of detectors to the reset signal generator; for each of the plurality of detectors, generating a reset signal by the reset signal generator based on the first feedback data; transmitting the reset signal by the reset signal generator to each of the plurality of detectors; and executing a clock synchronization in each of the plurality detectors based on the reset signal.

In some embodiments, for each of the set of preliminary reset signals, the generating first feedback data by each of the plurality of detectors may include for each of the set of preliminary reset signals, correspondingly generating a sequence of sampling values based on a sequence of clock cycle iteration with different phases; and taking the sequence of sampling values as the first feedback data.

In some embodiments, for each of the plurality of detectors, the generating a reset signal by the reset signal generator based on the first feedback data may include determining an optimum phase of the reset signal and generating the reset signal with the optimum phase. A sampling value of a preliminary reset signal, of the plurality of the preliminary reset signal, with the optimum phase may be positive. The sampling value may be predicted based on the clock cycle iteration with a zero phase.

In some embodiments, for each of the plurality of detectors, the generating a reset signal by the reset signal generator based on the first feedback data may include determining an optimum preliminary reset signal, of which a first value of the sequence of sampling values is positive; and generating the reset signal with the phase of the optimum preliminary reset signal.

In some embodiments, the method may further include generating second feedback data by each of the plurality of detectors based on the reset signal; transmitting the second feedback data by each of the plurality of detectors to the reset signal generator; determining, by the reset signal generator, whether the second feedback data corresponds to a predetermined value; and in response to determining that the second feedback value corresponds to the predetermined value, transmitting, by the reset signal generator, a determination instruction indicating that the reset signal has been correctly transmitted.

A still further aspect of the present disclosure relates to a non-transitory computer readable medium including executable instructions. When the executable instructions are executed by at least one processor, the executable instructions may direct the at least one processor to perform a method. The method may include generating, by a reset signal generator connected with a plurality of detectors, a set of preliminary reset signals, each of which has a different phase, to be detected; transmitting the set of preliminary reset signals by the reset signal generator to the plurality of detectors; for each of the set of preliminary reset signals, generating first feedback data by each of the plurality of detectors; transmitting the first feedback data by each of the plurality of detectors to the reset signal generator; for each of the plurality of detectors, generating a reset signal by the reset signal generator based on the first feedback data; transmitting the reset signal by the reset signal generator to each of the plurality of detectors; and executing a clock synchronization in each of the plurality detectors based on the reset signal.

A still further aspect of the present disclosure relates to a device for clock synchronization. The device may include a first synchronization component and one or more second synchronization components. The first synchronization component may be configured to transmit a first synchronization signal to the one or more second synchronization components. Each of the one or more second synchronization components may be configured to generate a second synchronization signal based on the first synchronization signal and transmit the second synchronization signal to one or more third synchronization components. Each of the one or more third synchronization components may be disposed in a detector and may be configured to reset a clock of the detector.

In some embodiments, a transmission time for transmitting the first synchronization signal from the first synchronization component to each of the one or more second synchronization components may be same.

In some embodiments, a transmission time for transmitting the second synchronization signal from each of the one or more second synchronization components to each of the one or more third synchronization components may be same.

In some embodiments, the first synchronization signal may include a synchronization clock signal and a synchronization reset signal.

In some embodiments, the first synchronization component may include a first buffer unit and one or more second buffer units. The first buffer unit may be configured to transmit the first synchronization signal to the one or more second buffer units. Each of the one or more second buffer units may be configured to transmit the first synchronization signal to the one or more second synchronization components.

In some embodiments, the second synchronization component may include a third buffer unit and one or more fourth buffer units. The third buffer unit may be configured to transmit the second synchronization signal to the one or more fourth buffer units. Each of the one or more fourth buffer units may be configured to transmit the second synchronization signal to the one or more third synchronization components.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
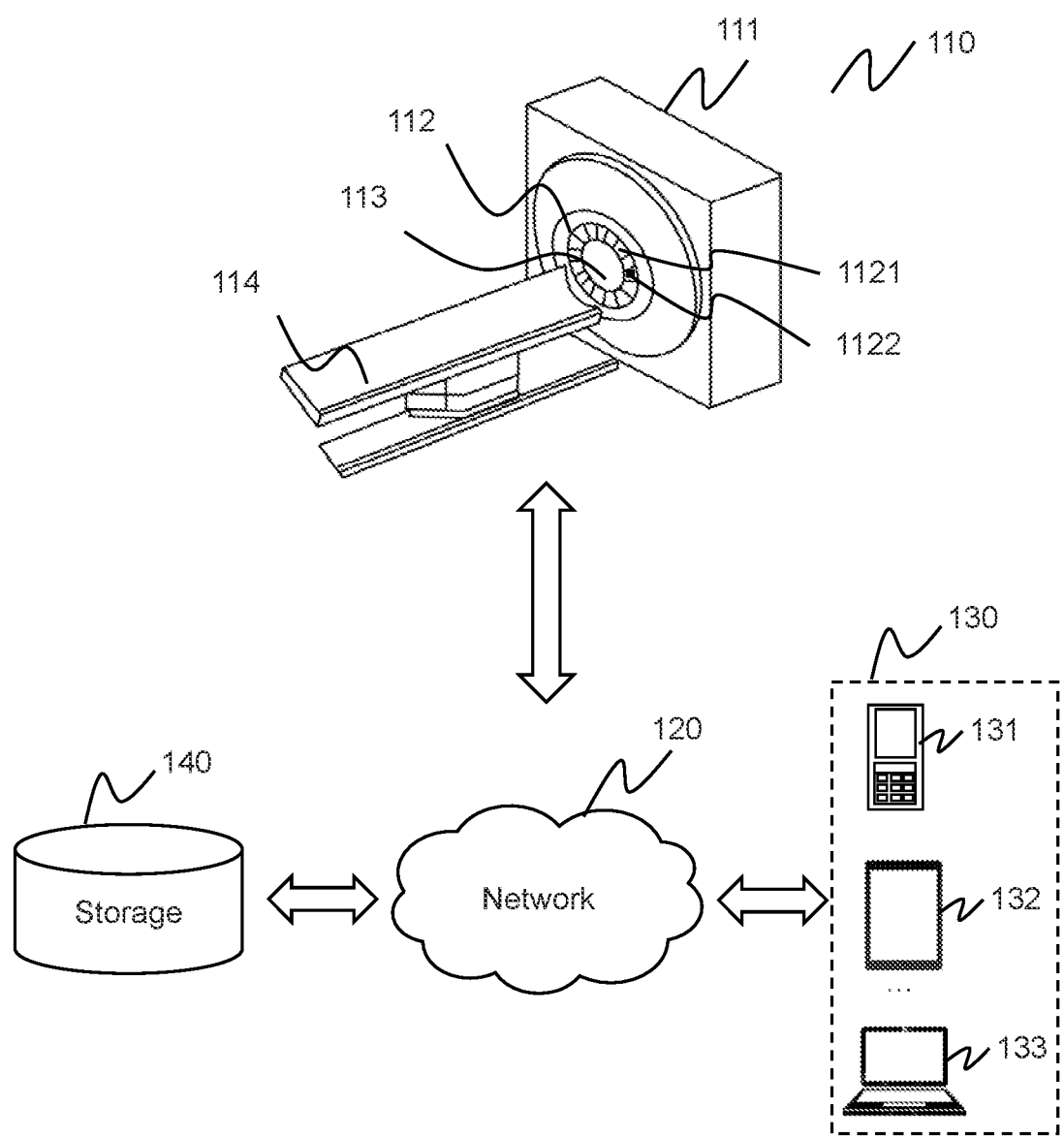
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the terms "system," "unit," "module," and/or "block" used herein are one method to distinguish different components, elements, parts, sections, or assemblies of different levels in ascending order. However, the terms may be displaced by another expression if they achieve the same purpose.

Generally, the words "module," "unit," or "block," as used herein, refer to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

Provided herein are systems and methods for non-invasive biomedical imaging/treatment, such as for disease diagnostic, disease therapy, or research purposes. In some embodiments, the systems may include an imaging device. The imaging device may include a single modality device (e.g., a positron emission tomography (PET) device) and/or a multi-modality device (e.g., a positron emission tomography-X-ray imaging (PET-X-ray) device, a positron emission tomography-computed tomography (PET-CT) device, a positron emission tomography-magnetic resonance imaging (PET-MR) device). The term "modality" used herein broadly refers to an imaging or treatment method or technology that gathers, generates, processes, and/or analyzes imaging information of a subject or treatments the subject. It should be noted that the medical device described below is merely provided for illustration purposes, and not intended to limit the scope of the present disclosure.

An aspect of the present disclosure relates to systems and methods for clock synchronization. The systems may include a reset signal generator connected with a plurality of detectors. The reset signal generator may be configured to generate a set of preliminary reset signals to be detected, each of the set of preliminary reset signals has a different phase, and transmit the set of preliminary reset signals to the plurality of detectors. Each of the plurality of detectors may be configured to generate first feedback data for each of the set of preliminary reset signals and transmit the first feedback data to the reset signal generator. The reset signal generator may be further configured to generate, for each of the plurality of detectors, a reset signal based on the first feedback data and transmit the reset signal to each of the plurality of detectors. Each of the plurality detectors may be further configured to execute a clock synchronization (e.g., simultaneously start the plurality of detectors' time counters or reset them to zero) in itself based on the reset signal.

According to the systems and methods of the present disclosure, the reset signal generated based on the set of preliminary reset signals can reduce or eliminate the unsynchronization of starting the plurality of detectors' time counters or resetting them to zero, which ensures that the plurality of detectors can simultaneously detect radiation rays (e.g., y rays), thereby improving the clarity and accuracy of the medical image of the patient obtained based on the detection of the plurality of detectors.

FIG. 1 is a schematic diagram illustrating an exemplary imaging system 100 according to some embodiments of the present disclosure. As shown, the imaging system 100 may include a scanner 110, a network 120, one or more terminals 130, and a storage device 140. In some embodiments, the scanner 110, the terminal(s) 130 and/or the storage device 140 may be connected to and/or communicate with each other via a wireless connection (e.g., the network 120), a wired connection, or a combination thereof. The connection between the components of the imaging system 100 may be variable. Merely by way of example, the scanner 110 may be connected to the storage device 140 through the network 120, as illustrated in FIG. 1, or connected to the storage device 140 directly. As another example, the scanner 110 may be connected to a terminal 130 through the network 120, as illustrated in FIG. 1, or connected to the terminal 130 directly.

The scanner 110 may generate or provide image data related to a subject via scanning the subject. In some embodiments, the subject may include a biological object and/or a non-biological object. For example, the subject may include a specific portion of a body, such as a head, a thorax, an abdomen, or the like, or a combination thereof. In some embodiments, the scanner 110 may include a single-modality scanner (e.g., a PET scanner) and/or multi-modality scanner (e.g., a PET-CT scanner, a PET-MRI scanner) as described elsewhere in this disclosure.

In some embodiments, the scanner 110 may include a gantry 111, a scanning device 112, a detecting region 113, and a scanning table 114. The gantry 111 may support the scanning device 112. The scanning device 112 may scan the subject on the scanning table 114. In some embodiments, the scanning device 112 may include a plurality of detectors 1121. The detectors 1121 may detect energy, time, and position information of radiation (e.g., gamma photons) emitted from the detection region 113. The detectors 1121 may be assembled in any suitable manner, for example, a ring, an arc, a rectangle, an array, or the like, or any combination thereof. Merely by way of example, the detectors 1121 may be located inside the scanning device 112 as shown in FIG. 1. Alternatively, the detectors 1121 may be worn on the body (e.g., a diseased location) of the subject. In some embodiments, each of the detectors 1121 may include a time counter 1122. The time counter 1122 may be used to record time information (e.g., a time cycle of the radiation emission) of the event detected by the corresponding detector. Time counters 1122 of the plurality of detectors 1121 may be simultaneously started or reset to synchronize the time information of the plurality of detectors 1121. The scanning table 114 may transport the subject into and out of, and facilitate the positioning of the subject in the detection region 113. In some embodiments, the detected radiation events may be stored or archived in a storage device (e.g., the storage device 140), displayed on a display, or transferred to an external storage device via a cable, or a wired or wireless network (e.g., the network 120). In some embodiments, a user may control the scanner 110 via the terminal(s) 130.

In some embodiments, the scanner 110 may be a PET scanner. Before scanning, a radioactive tracer isotope may be injected into the subject to be scanned. One or more atoms of the tracer isotope may be chemically incorporated into biologically active molecules in the subject. The active molecules may become concentrated in a tissue of interest within the subject. The tracer isotope may undergo positron emission decay and emit positrons. A positron may travel a short distance (e.g., about 1 mm) within a tissue of interest, lose kinetic energy, and interact with an electron of the subject. The position and the electron may annihilate and produce a pair of annihilation photons. The pair of annihilation photons (or radiation rays) may move in approximately opposite directions. A plurality of radiation rays may reach the scanning device 112 and be detected by the scanning device 112.

The network 120 may include any suitable network that can facilitate the exchange of information and/or data for the imaging system 100. In some embodiments, one or more components of the imaging system 100 (e.g., the scanner 110, the storage device 140, the terminal(s) 130) may communicate information and/or data with one or more other components of the imaging system 100 via the network 120. The network 120 may be or include a cable, a line on a circuit board, a connecting device, a channel, or the like, or any combination thereof.

The terminal(s) 130 may be connected to and/or communicate with the scanner 110 and/or the storage device 140. For example, the terminal(s) 130 may display a PET image of the subject. In some embodiments, the terminal(s) 130 may include a mobile device 131, a tablet computer 132, a laptop computer 133, or the like, or any combination thereof. For example, the mobile device 131 may include a mobile phone, a personal digital assistant (PDA), a gaming device, a navigation device, a point of sale (POS) device, a laptop, a tablet computer, a desktop, or the like, or any combination thereof. In some embodiments, the terminal(s) 130 may include an input device, an output device, etc.

The storage device 140 may store data, instructions, and/or any other information. In some embodiments, the storage device 140 may store data obtained from the terminal(s) 130 and/or the scanner 110. In some embodiments, the storage device 140 may store data and/or instructions that the scanner 110 (e.g., the plurality of detectors) may execute or use to perform exemplary methods described in the present disclosure. In some embodiments, the storage device 140 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 140 may be implemented on a cloud platform as described elsewhere in the disclosure.

In some embodiments, the storage device 140 may be connected to the network 120 to communicate with one or more other components of the imaging system 100 (e.g., the scanner 110, the terminal(s) 130). One or more components of the imaging system 100 may access the data or instructions stored in the storage device 140 via the network 120.

It should be noted that the above description of the imaging system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the imaging system 100 may include one or more additional components. Additionally or alternatively, one or more components of the imaging system 100 described above may be omitted. As another example, two or more components of the imaging system 100 may be integrated into a single component.

Figure 2:
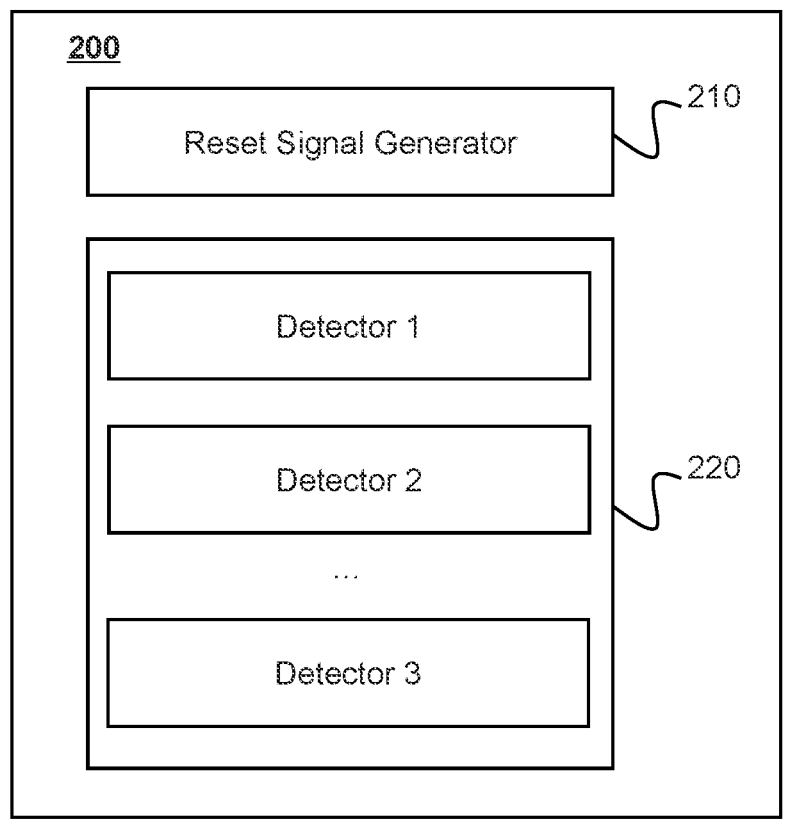
FIG. 2 is a block diagram illustrating an exemplary clock synchronization system according to some embodiments of the present disclosure.

FIG. 2 is a block diagram illustrating an exemplary clock synchronization system according to some embodiments of the present disclosure. The clock synchronization system 200 may include a reset signal generator 210 and a plurality of detectors 220 (e.g., a detector 1, a detector 2, a detector 3) connected to the reset signal generator 210.

The reset signal generator 210 may be configured to generate a set of preliminary reset signals to be detected. Each of the set of preliminary reset signals has a different phase. More descriptions regarding the generating of the set of preliminary reset signals may be found elsewhere in the present disclosure (e.g., operation 310 in FIG. 3 and the description thereof).

The reset signal generator 210 may be further configured to transmit the set of preliminary reset signals to the plurality of detectors (e.g., the detectors 1121). More descriptions regarding the transmitting of the set of preliminary reset signals may be found elsewhere in the present disclosure (e.g., operation 320 in FIG. 3 and the description thereof).

Each of the plurality of detectors 220 may be configured to generate first feedback data for each of the set of preliminary reset signals. In some embodiments, for each of the set of preliminary reset signals, each of the plurality of detectors 220 may correspondingly generate a sequence of sampling values based on a sequence of clock cycle iteration with different phases. Further, each of the plurality of detectors 220 may take the sequence of sampling values as the first feedback data. More descriptions regarding the generating of the first feedback data may be found elsewhere in the present disclosure (e.g., FIG. 5 and the description thereof).

Each of the plurality of detectors 220 may be further configured to transmit the first feedback data to the reset signal generator.

The reset signal generator 210 may be further configured to generate, for each of the plurality of detectors, a reset signal based on the first feedback data. In some embodiments, the reset signal generator 210 may determine an optimum phase of the reset signal. Further, the reset signal generator 210 may generate the reset signal with the optimum phase. In some embodiments, the reset signal generator 210 may determine an optimum preliminary reset signal, of which a first value of the sequence of sampling values is positive. Further, the reset signal generator 210 may generate the reset signal with the phase of the optimum preliminary reset signal. More descriptions regarding the generating of the reset signal may be found elsewhere in the present disclosure (e.g., FIG. 5 and the description thereof).

The reset signal generator 210 may be further configured to transmit the reset signal to each of the plurality of detectors.

Each of the plurality of detectors 220 may be further configured to execute a clock synchronization in itself based on the reset signal.

The modules in the clock synchronization system 200 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. In some embodiments, two or more of the modules may be combined into a single module, and any one of the modules may be divided into two or more units. In some embodiments, the processing device 120 may include one or more additional modules. For example, the clock synchronization system 200 may also include a transmission module (not shown) configured to transmit signals (e.g., electrical signals, electromagnetic signals) to one or more components (e.g., the terminal device 130, the storage device 140) of the medical system 100. As another example, the clock synchronization system 200 may include a storage module (not shown) used to store information and/or data (e.g., the set of preliminary reset signals with different phases, the first feedback data, the reset signal) associated with the clock synchronization.

Figure 3:
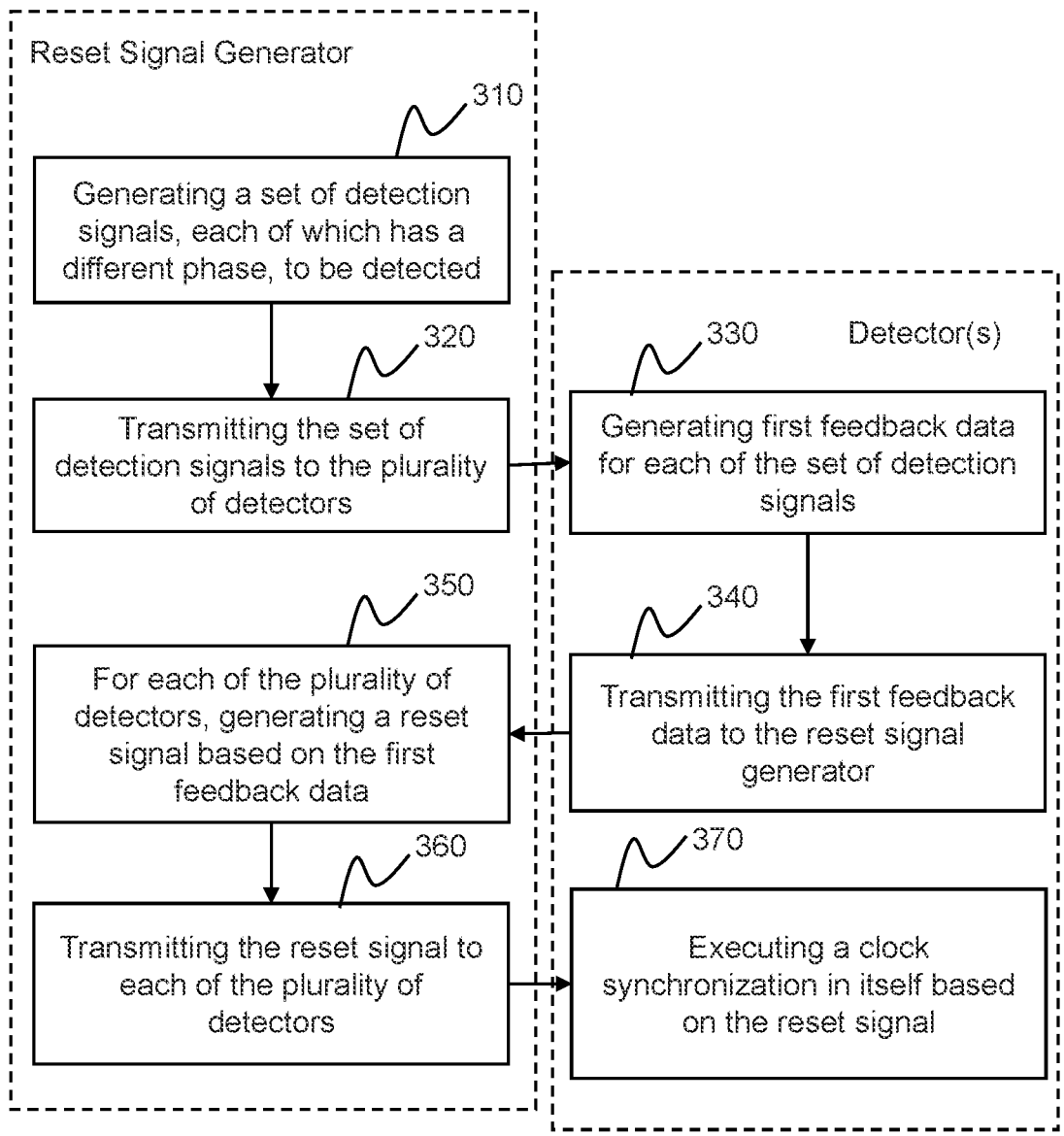
FIG. 3 is a flowchart illustrating an exemplary process for clock synchronization according to some embodiments of the present disclosure.

FIG. 3 is a flowchart illustrating an exemplary process for clock synchronization according to some embodiments of the present disclosure. In some embodiments, process 300 may be executed by the medical system 100. For example, the process 300 may be implemented as a set of instructions (e.g., an application) stored in a storage device (e.g., the storage device 140). In some embodiments, the clock synchronization system 200 (e.g., one or more modules illustrated in FIG. 2) may execute the set of instructions and may accordingly be directed to perform the process 300. The operations of the illustrated process presented below are intended to be illustrative. In some embodiments, the process 300 may be accomplished with one or more additional operations not described and/or without one or more of the operations discussed. Additionally, the order of the operations of process 300 illustrated in FIG. 3 and described below is not intended to be limiting.

In 310, the reset signal generator may generate a set of preliminary reset signals to be detected. Each of the set of preliminary reset signals has a different phase.

In some embodiments, the reset signal generator may refer to a circuit (e.g., an integrated circuit) for generating signals. Merely by way of example, the reset signal generator may include a field-programmable gate array (FPGA), a central processing unit (CPU), a graphics processing unit (GPU), a digital signal processor (DSP), an application-specific integrated circuit (ASIC), a system on chip (SOC), or the like, or any combination thereof. In some embodiments, the reset signal generator may be integrated into the scanner 110. For example, the reset signal generator may be integrated on a circuit board of the scanner 110.

In some embodiments, a preliminary reset signal may refer to a pulse signal with at least one down edge. More descriptions regarding the preliminary reset signals may be found elsewhere in the present disclosure (e.g., FIG. 4 and the description thereof). In some embodiments, each of the set of preliminary reset signals may have a phase. More descriptions regarding phases of the preliminary reset signals may be found elsewhere in the present disclosure (e.g., FIG. 4 and the description thereof). A phase of each of the set of preliminary reset signals is different from phases of other preliminary reset signals in the set of preliminary reset signals. A phase of one of the set of preliminary reset signals may be the same as a phase of a preliminary reset signal in other sets of preliminary reset signals. In some embodiments, a count of preliminary reset signals in the set of preliminary reset signals may be a default setting (e.g., 4, 6, 9) of the reset signal generator, or set by a user manually, or by the reset signal generator according to an actual need.

In 320, the reset signal generator may transmit the set of preliminary reset signals to the plurality of detectors (e.g., the detectors 1121). In some embodiments, the reset signal generator may transmit the set of preliminary reset signals via a network (e.g., the network 120). As described in connection with FIG. 1, the network 120 may be or include a cable, a line on a circuit board, a connecting device, a channel, or the like, or any combination thereof.

In 330, each of the plurality of detectors may generate first feedback data for each of the set of preliminary reset signals. In some embodiments, the first feedback data may be a sequence consisting of 0 and 1, such as 1100, 0110, 0011, 111000, 110011, etc.

In some embodiments, for each of the set of preliminary reset signals, each of the plurality of detectors may correspondingly generate a sequence of sampling values based on a sequence of clock cycle iteration with different phases. Further, each of the plurality of detectors may take the sequence of sampling values as the first feedback data. More descriptions regarding the generating of the first feedback data may be found elsewhere in the present disclosure (e.g., FIG. 5 and the description thereof).

In some embodiments, each of the plurality of detectors may perform detection based on a frequency higher than a standard clock frequency and obtain a time difference between the preliminary reset signal and the standard clock cycle. Further, each of the plurality of detectors may designate the time difference as the first feedback data.

In 340, each of the plurality of detectors may transmit the first feedback data to the reset signal generator. In some embodiments, each of the plurality of detectors may transmit the first feedback data via the network described in operation 320.

In 350, for each of the plurality of detectors, the reset signal generator may generate a reset signal based on the first feedback data. In some embodiments, the reset signal may be one of the plurality of preliminary reset signals. For example, the reset signal may be a preliminary reset signal with an optimal phase.

In some embodiments, the reset signal generator may determine an optimum phase of the reset signal. A sampling value of a preliminary reset signal, of the plurality of the preliminary reset signal, with the optimum phase is positive. The sampling value is predicted based on a clock cycle iteration with a zero phase. Further, the reset signal generator may generate the reset signal with the optimum phase. More descriptions regarding the generating of the reset signal with the optimum phase may be found elsewhere in the present disclosure (e.g., FIG. 5 and the description thereof).

In some embodiments, the reset signal generator may determine an optimum preliminary reset signal, of which a first value of the sequence of sampling values is positive. Further, the reset signal generator may generate the reset signal with the phase of the optimum preliminary reset signal. For example, the reset signal generator may designate the optimum preliminary reset signal as the reset signal. More descriptions regarding the generating of the reset signal with the phase of the optimum preliminary reset signal may be found elsewhere in the present disclosure (e.g., FIG. 5 and the description thereof).

In some embodiments, the reset signal generator may generate the reset signal based on the time difference described in operation 330. For example, the reset signal generator may select a preliminary reset signal corresponding to a minimum time difference from the set of preliminary reset signals as the reset signal.

In 360, the reset signal generator may transmit the reset signal to each of the plurality of detectors. In some embodiments, the reset signal generator may transmit the reset signal via the network described in operation 320.

In some embodiments, each of the plurality of detectors may generate second feedback data based on the reset signal from each of the plurality of detectors. As used herein, the second return data may refer to data generated by a detector in response to receiving the reset signal. Merely by way of example, the detector may extract a characteristic (e.g., a phase) of the reset signal as the second return data. Each of the plurality of detectors may transmit the second feedback data to the reset signal generator. Each of the plurality of detectors may transmit the second feedback data via the network described in operation 320. After receiving the second feedback data, the reset signal generator may determine whether the second feedback data corresponds to a predetermined value. The predetermined value may be default settings of the reset signal generator or may be adjustable under different situations. Merely by way of example, the reset signal generator may determine whether the second feedback data is equal to the predetermined value. If the second feedback data is equal to the predetermined value, the reset signal generator may determine that the second feedback data corresponds to a predetermined value. In response to determining that the second feedback value corresponds to the predetermined value, the reset signal generator may transmit a determination instruction indicating that the reset signal has been correctly transmitted. In some embodiments, the reset signal generator may transmit the determination instruction via the network described in operation 320. After receiving the determination instruction, each of the plurality detectors may perform operation 370. In this embodiment, whether the reset signal has been correctly transmitted is verified, which ensures the accuracy of the reset signal received by each detector, thereby improving the accuracy that time counters of the plurality of detectors are started or reset simultaneously.

In 370, each of the plurality detectors may execute a clock synchronization in itself based on the reset signal.

In some embodiments, when a reset signal is received, time counters (e.g., the time counter 1122) of the plurality of detectors may be simultaneously started or reset to synchronize time information of the plurality of detectors (e.g., the detectors 1121). In the present disclosure, the reset signal generated based on the set of preliminary reset signals can reduce or eliminate the unsynchronization of starting the plurality of detectors' time counters or resetting them to zero, which ensures that the plurality of detectors can simultaneously detect radiation rays (e.g., y rays), thereby improving the clarity and accuracy of the medical image of the patient obtained based on the detection of the plurality of detectors.

It should be noted that the above description regarding the process 300 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 300 may be accomplished with one or more additional operations not described and/or without one or more of the operations discussed above. For example, the process 300 may include an additional storing operation in which the signal generator and/or the plurality of detectors may store information and/or data (e.g., the set of preliminary reset signals with different phases, the first feedback data, the reset signal) associated with clock synchronization in a storage device (e.g., the storage device 140) disclosed elsewhere in the present disclosure.

Figure 4:
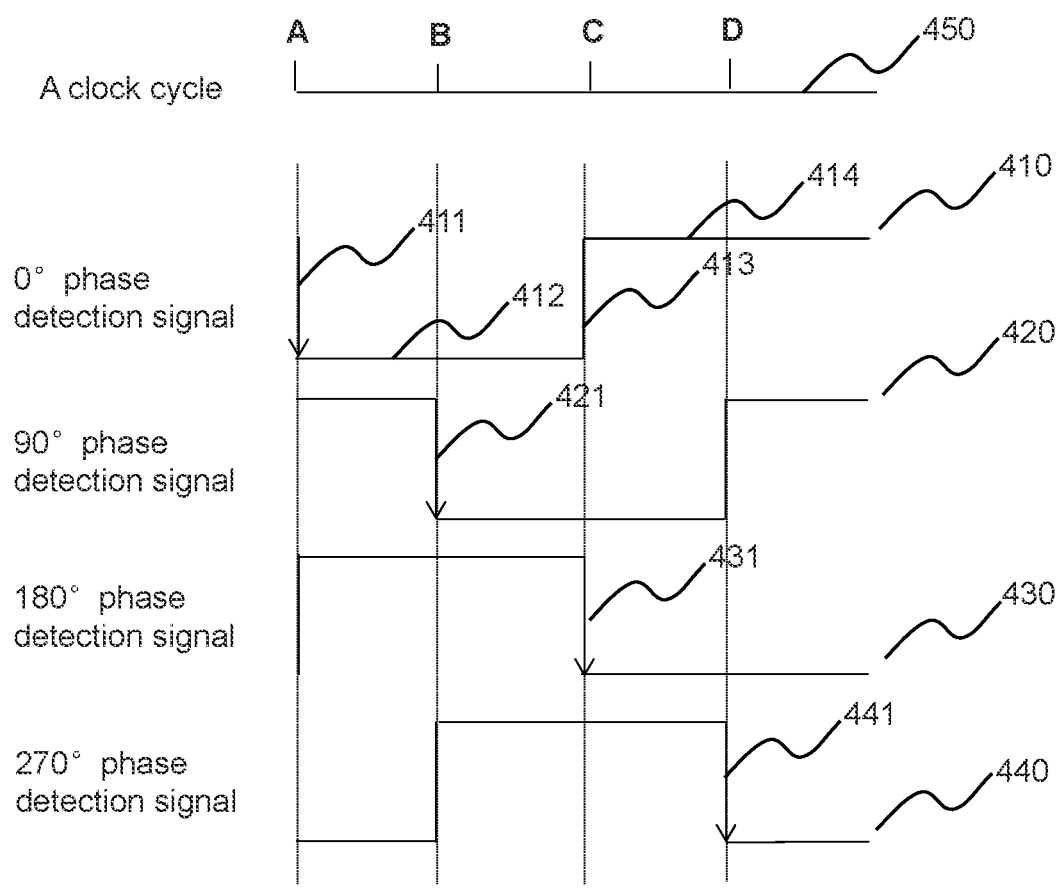
FIG. 4 is a schematic diagram illustrating exemplary preliminary reset signals according to some embodiments of the present disclosure.

FIG. 4 is a schematic diagram illustrating exemplary preliminary reset signals according to some embodiments of the present disclosure. As described in connection with FIG. 3, a preliminary reset signal may refer to a pulse signal with at least one down edge (e.g., 411).

In some embodiments, as illustrated in FIG. 4, a preliminary reset signal (e.g., 410, 420, 430, 440) may include a complete pulse period. For example, a pulse period of the preliminary reset signal 410 may include a down edge 411, a low edge 412, an up edge 413, and a top edge 414 (also referred to as a "valid edge"). The down edge 411 and the up edge 413 may be referred to as a jump edge. As used herein, the down edge may refer to a moment when the pulse signal jumps from a high electrical level to a low electrical level. The low edge may refer to a time period when the pulse signal is at the low electrical level. The up edge may refer to a moment when the pulse signal jumps from the low electrical level to the high electrical level. The top edge may refer to a time period when the pulse signal is at the high electrical level.

In some embodiments, a phase of a preliminary reset signal may be determined based on a relationship between a pulse signal of the preliminary reset signal and a clock cycle. As used herein, the clock cycle may refer to the smallest unit of time in a computer. In one clock cycle (e.g., 10 nanoseconds, 5 nanoseconds), a CPU only completes one most basic action. For example, as illustrated in FIG. 4, assuming that a clock cycle 450 is used to determine a phase of a preliminary reset signal. When a down edge (e.g., 411) of a preliminary reset signal (e.g., 410) corresponds to a beginning position A of the clock cycle 450, a phase of the preliminary reset signal (e.g., 410) may be regarded as 0°; when a down edge (e.g., 421) of a preliminary reset signal (e.g., 420) corresponds to a 0.25 cycle position B phase of the clock cycle, a phase of the preliminary reset signal (e.g., 420) may be regarded as 90°; when a down edge (e.g., 431) of a preliminary reset signal (e.g., 430) corresponds to a 0.5 cycle position C of the clock cycle, a phase of the preliminary reset signal (e.g., 430) may be regarded as 180°; when a down edge (e.g., 441) of a preliminary reset signal (e.g., 440) corresponds to a 0.75 cycle position D of the clock cycle, a phase of the preliminary reset signal (e.g., 440) may be regarded as 270°. In some embodiments, a reset signal generator may generate a first preliminary reset signal (e.g., 410) with a 0° phase, a second preliminary reset signal (e.g., 420) with a 90° phase, a third preliminary reset signal (e.g., 430) with a 180° phase, and a fourth preliminary reset signal (e.g., 440) with a 270° phase. It should be noted that the above description regarding the determining of a phase of a preliminary reset signal is merely provided for illustration purposes, and not intended to limit the scope of the present disclosure.

Figure 5:
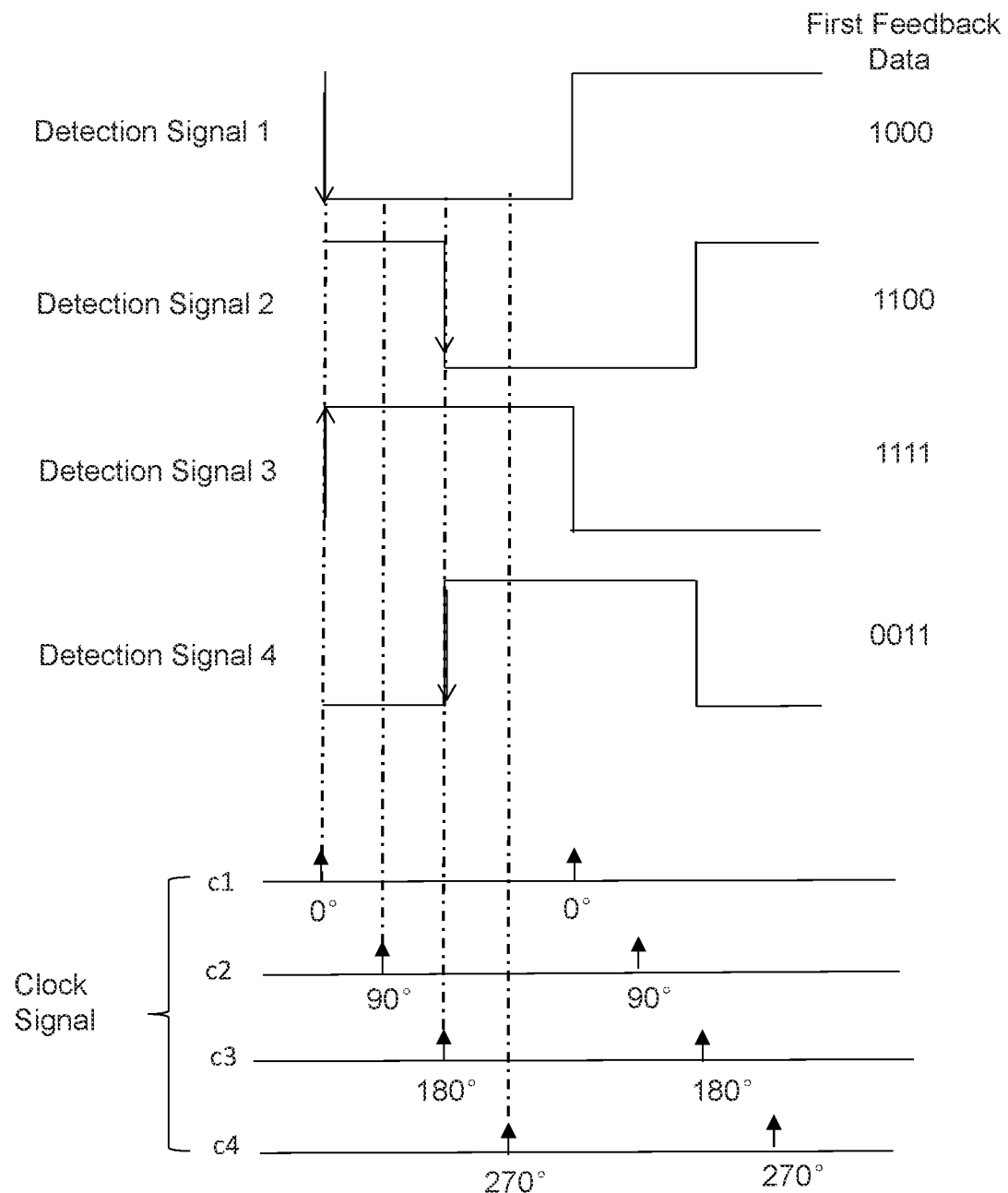
FIG. 5 is a schematic diagram illustrating exemplary operations for generating first feedback data according to some embodiments of the present disclosure.

FIG. 5 is a schematic diagram illustrating exemplary operations for generating first feedback data according to some embodiments of the present disclosure.

As described in connection with FIG. 3, for each of the set of preliminary reset signals, each of the plurality of detectors may correspondingly generate a sequence of sampling values based on a sequence of clock cycle iteration with different phases. In some embodiments, a detector may generate a plurality of clock signals with different phases, for example, a clock signal C1 with a 0° phase, a clock signal C2 with a 90° phase, a clock signal C3 with a 180° phase, and a clock signal C4 with 270° phase illustrated in FIG. 5. As used herein, a clock signal may refer to a signal with a fixed clock frequency, wherein the clock frequency is a reciprocal of a clock cycle. In some embodiments, a phase of a clock signal may indicate a relative time relationship between the clock signal and a standard clock signal. When a clock signal is synchronized with the standard clock signal, a phase of the clock signal may be 0°; when the clock signal lags 0.25 cycles relative to the standard clock signal, the phase of the clock signal may be 90°; when the clock signal lags 0.5 cycles relative to the standard clock signal, the phase of the clock signal may be 180°; when the clock signal lags 0.75 cycles relative to the standard clock signal, the phase of the clock signal may be 270°. It should be noted that the above description regarding the determining of phases of the clock signal is merely provided for illustration purposes, and not intended to limit the scope of the present disclosure.

Further, the detector may sample a preliminary reset signal based on the plurality of clock signals (e.g., C1, C2, C3, and C4) to generate a sequence of sampling values of the preliminary reset signal. As described in connection with FIG. 4, a pulse period of the preliminary reset signal may include a down edge, a low edge, an up edge, and a top edge. In some embodiments, the down edge, the up edge, and the top edge may indicate a high electrical level value in the pulse signal and the low edge may indicate a low electrical level value in the pulse signal. In the present disclosure, "positive" is used to indicate the high electrical level value. The "positive" may be expressed in a variety of convenient forms. For example, "1" may be used to express the "positive". The detector may sample the preliminary reset signal based on the plurality of clock signals (e.g., C1, C2, C3, and C4) and electrical level values of the preliminary reset signal.

For example, as illustrated in FIG. 5, the detector may sample a preliminary reset signal 1 based on the clock signal C1, C2, C3, and C4. Specifically, when the clock signal C1 is used to sample the preliminary reset signal 1, the detector may sample the down edge of the preliminary reset signal 1 and obtain a sampling value between 0-1, for example, 0.6. When the clock signal C2, C3, and C4 are used to sample the preliminary reset signal 1 respectively, the detector may sample the low edge of the preliminary reset signal 1 and obtain a sampling value 0. Merely by way of example, the obtained sampling value may be further processed. For example, the detector may convert the sampling value between 0-1 to other forms. As another example, the detector may convert the sampling value (e.g., 0.6) greater than 0.5 to 1 and the sampling value (e.g., 0.3) less than 0.5 to 0. Then, the detector may obtain a sequence 1000 of the above sampling values and take the sequence 1000 as first feedback data of the preliminary reset signal 1.

As another example, as illustrated in FIG. 5, the detector may sample a preliminary reset signal 2 based on the clock signal C1, C2, C3, and C4. Specifically, when the clock signal C1 and C2 are used to sample the preliminary reset signal 2 respectively, the detector may sample the top edge of the preliminary reset signal 2 and obtain a sampling value 1. When the clock signal C3 is used to sample the preliminary reset signal 2, the detector may sample the down edge of the preliminary reset signal 2 and obtain a sampling value between 0-1, for example, 0.3. When the clock signal C4 is used to sample the preliminary reset signal 2, the detector may sample the low edge of the preliminary reset signal 2 and obtain a sampling value 0. Then, the detector may obtain a sequence 1100 of the above sampling values and take the sequence 1100 as first feedback data of the preliminary reset signal 2.

In some embodiments, when the detector samples a preliminary reset signal based on nine clock signals, the generated sequence of sampling values may consist of nine digits, for example, 000111000, 111000000, 000000111, etc.

The reset signal generator may determine an optimum phase of the reset signal. For example, sampling values of the preliminary reset signal 1, the preliminary reset signal 2, the preliminary reset signal 3, and the preliminary reset signal 4 may be determined based on a clock signal (e.g., C1) with a zero phase (e.g., the 0° phase). According to the above description of operation 320, the sampling values of the preliminary reset signal 1 and the preliminary reset signal 2 with respect to the clock signal C1 are 1. According to the operation for sampling the preliminary reset signal in the above description of operation 320, the sampling values of the preliminary reset signal 3 and the preliminary reset signal 4 with respect to the clock signal C1 may be determined as 1 and 0 respectively. The sequence of sampling values of the preliminary reset signal 1, the preliminary reset signal 2, the preliminary reset signal 3, and the preliminary reset signal 4 is 1110. The reset signal generator may determine the optimum phase of the reset signal based on the sequence of sampling values of the preliminary reset signal 1, the preliminary reset signal 2, the preliminary reset signal 3, and the preliminary reset signal 4. It can be seen from the sequence 1110 that the sampling value of the preliminary reset signal 3 and the sampling value of preliminary reset signal 4 are different while the sampling value of the preliminary reset signal 1 and the sampling value of preliminary reset signal 2 are the same, which indicates the instability of preliminary reset signals with phases between the phase (180°) of the preliminary reset signal 3 and the phase (270°) of preliminary reset signal 4 and the stability of preliminary reset signals with phases between the phase (0°) of the preliminary reset signal 1 and the phase (90°) of preliminary reset signal 2. Further, the reset signal generator may select a phase (e.g., 45°) from the phases between the phase (0°) of the preliminary reset signal 1 and the phase (90°) of preliminary reset signal 2 as the optimum phase of the reset signal and generate the reset signal with the optimum phase.

The reset signal generator may determine an optimum preliminary reset signal, of which a first value of the sequence of sampling values is positive (e.g., 1). For example, sequences of sampling values of the preliminary reset signal 1, the preliminary reset signal 2, the preliminary reset signal 3, and the preliminary reset signal 4 are 1000, 1100, 1111, and 0011 respectively. First values of the sequences of sampling values 1000, 1100, and 1111 are positive. In some embodiments, the reset signal generator may arbitrarily select a preliminary reset signal with a positive first value as the optimum preliminary reset signal. For example, the reset signal generator may arbitrarily select a preliminary reset signal from the preliminary reset signal 1, the preliminary reset signal 2, and the preliminary reset signal 3 as the optimum preliminary reset signal. Preferably, the reset signal generator may select a preliminary reset signal (e.g., the preliminary reset signal 2, the preliminary reset signal 3) with a plurality of positive sampling values as the optimum preliminary reset signal. For example, the reset signal generator may select the preliminary reset signal 3 with four positive sampling values as the optimum preliminary reset signal. Further, the reset signal generator may generate the reset signal with the phase of the optimum preliminary reset signal.

In the following description, a pending reset signal may be an example of a preliminary reset signal. A first return signal and a first return value may be an example of first feedback data. A second return signal may be an example of second feedback data. A preset return value may be an example of a predetermined value. A rough time counter may be an example of a time counter.

Figure 6:
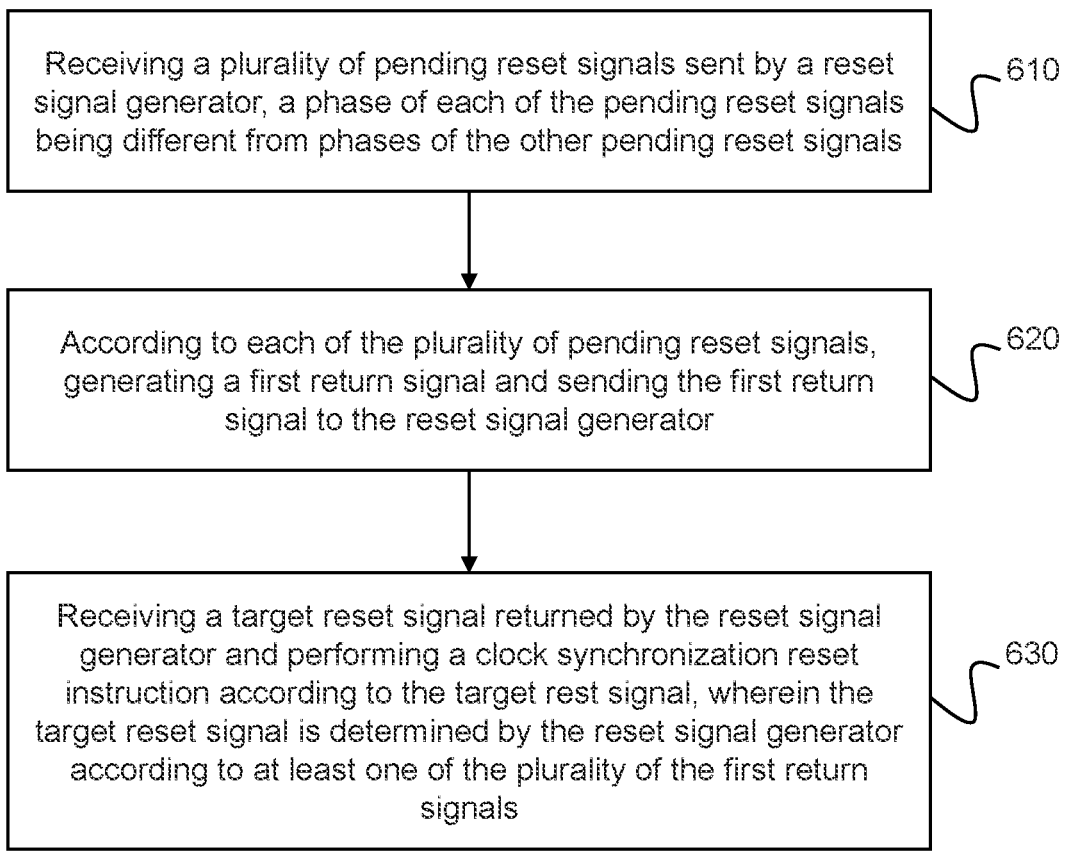
FIG. 6 is a flowchart illustrating an exemplary process for clock synchronization executed by one or more detectors according to some embodiments of the present disclosure.

FIG. 6 is a flowchart illustrating an exemplary process for clock synchronization executed by one or more detectors according to some embodiments of the present disclosure. In some embodiments, process 600 may be executed by the medical system 100. For example, the process 600 may be implemented as a set of instructions (e.g., an application) stored in a storage device (e.g., the storage device 150). In some embodiments, the clock synchronization system 200 (e.g., one or more modules illustrated in FIG. 2) may execute the set of instructions and may accordingly be directed to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting.

In 610, one or more detectors 602 may receive a plurality of pending reset signals sent by a reset signal generator 601. A phase of each of the pending reset signals may be different from the phases of the other pending reset signals.

Each of the one or more detectors 602 may receive the plurality of pending reset signals through an information sending channel. For example, the detector 602 may receive a first pending reset signal, a second pending reset signal, and a (N−1)th pending reset signal through the information sending channel.

In 620, according to each of the plurality of pending reset signals, the one or more detectors 602 may generate a first return signal and send the first return signal to the reset signal generator 601. When the detector 602 receives one pending reset signal with specific phase information, the detector 602 may detect the phase of the pending reset signal and generate the first return signal based on the phase. Further, the detector 602 may send the first return signal to the reset signal generator 601 through an information feedback channel. Merely by way of example, the first return signal may be a binary value.

In some embodiments, the one or more detectors 602 may generate a plurality of clock signals having the same frequency (thereafter, referred to as "same frequency clock signals," and the same is applied to other similar terms). Each of the plurality of same frequency clock signals may correspond to one of the pending reset signals. A phase value of the pending reset signal may be the same as a phase value of its corresponding same frequency clock signal. Based on the same frequency clock signal corresponding to the pending reset signal, the one or more detectors 602 may sample the pending reset signal to generate the return signal of the first pending reset signal. Further, the one or more detectors 602 may send the first return signal to the reset signal generator 601. When the count of the pending reset signal is N−1, the count of the same frequency clock signal may be also N−1. According to a positional relationship between the pending reset signal and the corresponding same frequency clock signal corresponding, the one or more detectors 602 may generate a first return signal of the pending reset signal. The first return signal may be a value returned to the reset signal generator 601 by the one or more detectors 602.

In 630, the one or more detectors 602 may receive a reset signal returned by the reset signal generator 601, wherein the reset signal may be determined by the reset signal generator 601 according to at least one of the plurality of the first return signals. Further, the one or more detectors 602 may execute a clock synchronization reset instruction according to the rest signal. The reset signal may be a reset signal with the optimal phase determined by the reset signal generator 601. For example, when the detector 602 receives the first pending reset signal, the second pending reset signal, . . . and the (N−1)th pending reset signal through the information sending channel, the detector 602 may generate the N−1 first return signals and send the N−1 first return signals to the reset signal generator 601. The reset signal generator 601 may receive the N−1 first return signals and determine the reset signal according to the received N−1 first reset signals. In some embodiments, after determining the reset signal, the reset signal generator 601 may no longer receive or determine the subsequent return signals. For example, when receiving a second return signal and determining the reset signal based on the first return signal and the second return signal, the reset signal generator 601 may no longer receive the (N−1)th return signal. The reset signal generator 601 may send the reset signal to the one or more detectors 602. Further, time counter(s) of the one or more detectors 602 may simultaneously execute a clear instruction to resetting the time counter(s) to zero. In some embodiments, the reset signal may be one of the N−1 pending reset signals.

In some embodiments, the reset signal generator 601 may send the pending reset signals with a plurality of different phases. The detector 602 may detect the phase information of effective edges of each pending reset signal and send the phase information to the reset signal generator 601. The reset signal generator 601 may select the optimal phase from the transmitted pending reset signal phases according to the phase information, and send the pending reset signal (i.e., the reset signal) corresponding to the optimal phase to the detector 602, which may guarantee that the one or more detectors 602 may securely reset the time counters to zero in a same cycle, thereby achieving the synchronization of the one or more detectors 602. In the case that reset channels of the one or more detectors 602 have a certain difference, the scheme of the present disclosure may ensure that the time counters of the one or more detectors 602 may be started and reset at the same time.

In some embodiments, before the clock synchronization reset instruction is executed, according to the reset signal, the one or more detectors 602 may generate the second return signal and send the second return signal to the reset signal generator 601. Further, the one or more detectors 602 may receive a determination instruction returned by the reset signal generator 601, wherein the determination instruction may be determined by the reset signal generator 601 according to the second return signal. The determination instruction may be used to determine whether the reset signal has been sent correctly. The second return signal may be a binary value. In some embodiments, when the reset signal generator 601 confirms that an Nth phase has been correctly transmitted according to the second return signal, the reset signal generator 601 may send the determination instruction that the reset signal has been correctly transmitted. When the determination instruction is received, the time counters of the one or more detectors 602 may execute the simultaneous reset instruction. In the embodiment, the determination instruction may ensure the correctness of the reset signal received by the detector 602 and that the time counter of the detector 602 may be reset to zero and started at the same time.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 600 may be accomplished with one or more additional operations not described and/or without one or more of the operations discussed above.

Figure 7:
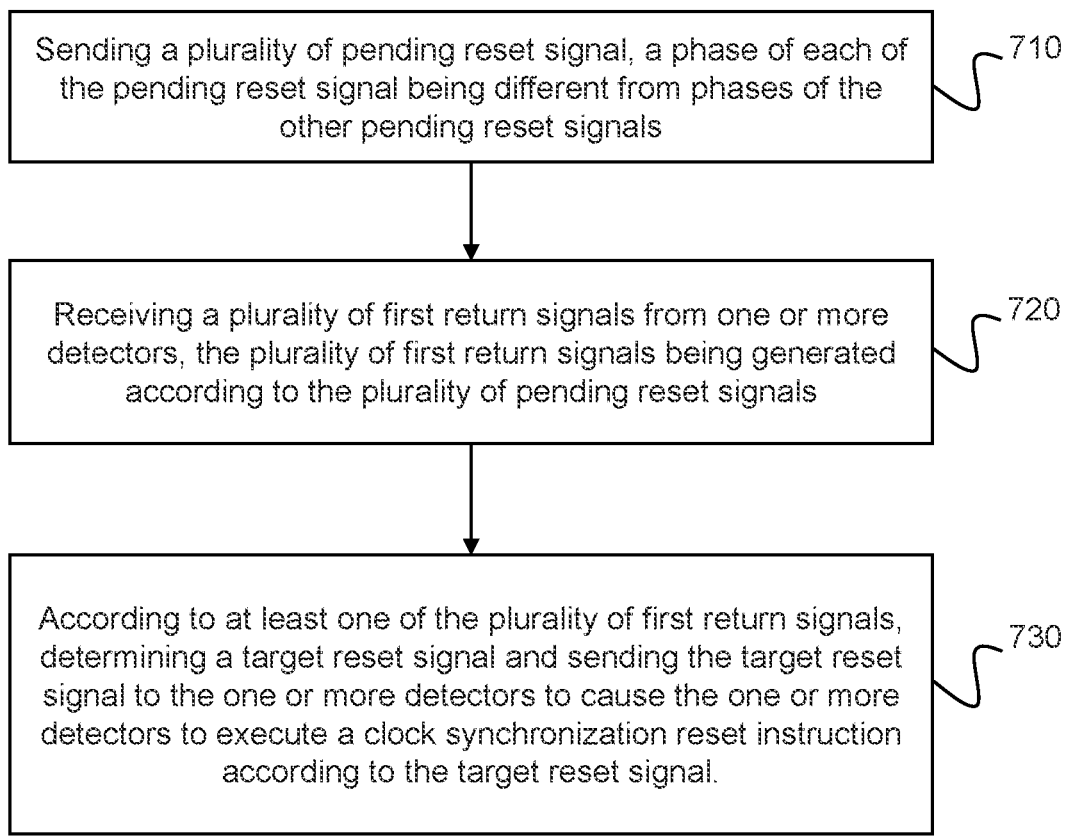
FIG. 7 is a flowchart illustrating an exemplary process for clock synchronization executed by a reset signal generator according to some embodiments of the present disclosure.

FIG. 7 is a flowchart illustrating an exemplary process for clock synchronization executed by a reset signal generator according to some embodiments of the present disclosure. In some embodiments, process 700 may be executed by the medical system 100. For example, the process 700 may be implemented as a set of instructions (e.g., an application) stored in a storage device (e.g., the storage device 150). In some embodiments, the clock synchronization system 200 (e.g., one or more modules illustrated in FIG. 2) may execute the set of instructions and may accordingly be directed to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting.

In 710, the reset signal generator 601 may send a plurality of pending reset signals. A phase of each of the pending reset signals may be different from phases of the other pending reset signals.

In some embodiments, the reset signal generator 601 may send the plurality of pending reset signals through an information sending channel. For example, the reset signal generator 601 may send a first pending reset signal, a second pending reset signal, and a (N−1)th pending reset signal through the information sending channel.

In 720, the reset signal generator 601 may receive a plurality of first return signals 602 from one or more detectors. The plurality of first return signals may be generated by the one or more detectors 602 according to the plurality of pending reset signals. When the detector 602 receives one pending reset signal with specific phase information, the detector 602 may detect the phase of the pending reset signal and generate the first return signal based on the phase. Further, the detector 602 may send the first return signal to the reset signal generator 601 through an information feedback channel. Merely by way of example, the first return signal may be a binary value.

In 730, according to at least one of the plurality of first return signals, the reset signal generator 601 may determine a reset signal and send the reset signal to the one or more detectors 602. The one or more detectors 602 may execute a clock synchronization reset instruction according to the reset signal. The reset signal generator 601 may receive the N−1 first return signals and determine the reset signal according to the received N−1 first reset signals. In some embodiments, the reset signal may be one of the N−1 pending reset signals. The reset signal generator 601 may send the reset signal to the one or more detectors 602. Further, time counter(s) of the one or more detectors 602 may simultaneously execute a clear instruction to resetting the time counter(s) to zero.

In some embodiments, the reset signal generator 601 may send the pending reset signals with a plurality of different phases. The detector 602 may detect the phase information of effective edges of each pending reset signal and send the phase information to the reset signal generator 601. The reset signal generator 601 may select the optimal phase from the transmitted pending reset signal phases according to the phase information, and send the pending reset signal (i.e., the reset signal) corresponding to the optimal phase to the detector 602, which may guarantee that the one or more detectors 602 may securely reset the time counters to zero in a same cycle, thereby achieving the synchronization of the one or more detectors 602. In the case that reset channels of the one or more detectors 602 have a certain difference, the scheme of the present disclosure may ensure that the time counters of the one or more detectors 602 may be started and reset at the same time.

In some embodiments, for each of the plurality of first return signals, the reset signal generator 601 may determine whether the first return signal corresponds to a preset return value. In response to that the first return signal corresponds to the preset return value, the reset signal generator 601 may determine that the pending reset signal corresponding to the first return signal is the reset signal. The preset return value may be set according to a positional relationship between the pending reset signal and a same frequency clock signal corresponding to the pending reset signal. The reset signal generator 601 may select the optimal phase from the transmitted pending reset signal phases according to the phase information, and send the pending reset signal (i.e., the reset signal) corresponding to the optimal phase to the detector 602, which may guarantee that the one or more detectors 602 may securely reset the time counters to zero in a same cycle, thereby achieving the synchronization of the one or more detectors 602.

In some embodiments, after the reset signal is sent to the detector 602, the reset signal generator 601 may receive a second return signal sent by the one or more detectors 602. The second return signal may be generated by the one or more detectors 602 according to the reset signal. Further, the reset signal generator 601 may determine whether the second return signal corresponds to the preset return value. In response to that the second return signal corresponds to the preset return value, the reset signal generator 601 may send a determination instruction, that the reset signal has sent correctly, to the one or more detectors 602. When the determination instruction is received, the time counters of the one or more detectors 602 may execute the simultaneous reset instruction. In the embodiment, the determination instruction may ensure the correctness of the reset signal received by the detector 602 and that the time counter of the detector 602 may be reset to zero and started at the same time.

It should be noted that the above description regarding the process 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 700 may be accomplished with one or more additional operations not described and/or without one or more of the operations discussed above.

Figure 8:
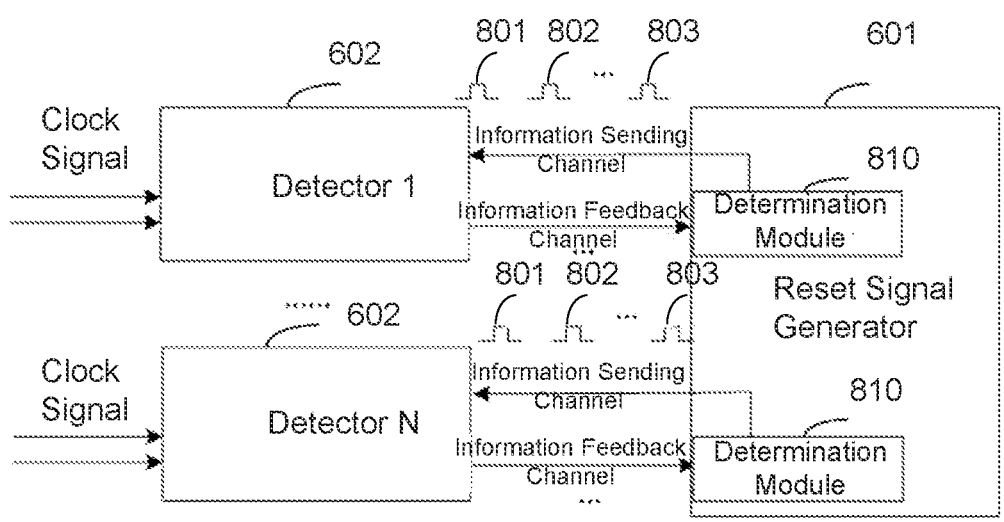
FIG. 8 is a schematic diagram illustrating an exemplary clock synchronization device according to some embodiments of the present disclosure.

FIG. 8 is a schematic diagram illustrating an exemplary clock synchronization device according to some embodiments of the present disclosure. The clock synchronization device may include a reset signal generator 601 and one or more detectors 602.

The reset signal generator 601 may be configured to send a plurality of pending reset signal. A phase of each of the pending reset signals may be different from the phases of all the other pending reset signals. The one or more detectors 602 (e.g., detector 1, detector N) may be connected to the reset signal generator 601. The one or more detector 602 may receive the plurality of pending reset signals sent by the reset signal generator 601, and generate a plurality of return signals according to the plurality of first pending reset signals. Further, the one or more detectors 602 may send the plurality of first return signals to the reset signal generator 601. The reset signal generator 601 may receive the plurality of first return signals and determine at least one reset signal according to the plurality of first return signals. Then, the reset signal generator 601 may send the reset signal to the one or more detectors 602. The one or more detectors 602 may receive the reset signal and execute a clock synchronization reset instruction according to the reset signal.

In some embodiments, the PET-CT system may include the plurality of detectors 602. The reset signal generator 601 may be connected with the plurality of detectors 602. Only by way of example, the reset signal generator 601 and each of the detectors 602 may perform an information interaction through an information sending channel and an information feedback channel. Each of the detectors 602 may receive the plurality of pending reset signals through the information sending channel. For example, the detector 602 may receive a first pending reset signal 801, a second pending reset signal 802, and a (N−1)th pending reset signal 803 through the information sending channel.

When each of the detectors 602 receives one pending reset signal with specific phase information, the detector 602 may obtain the phase of the pending reset signal and generate the first return signal based on the phase. Further, the detector 602 may send the first return signal to the reset signal generator 601 through an information feedback channel. Merely by way of example, the first return signal may be a binary value. The reset signal generator 601 may determine the reset signal according to the received N−1 first return signals. In some embodiments, the reset signal may be one of the N−1 pending reset signals. The reset signal may be a reset signal with the optimal phase determined by the reset signal generator 601. The reset signal generator 601 may send the reset signal to the one or more detectors 602. Further, time counter(s) of the one or more detectors 602 may simultaneously execute a clear instruction to resetting the time counter(s) to zero.

In some embodiments, the reset signal generator 601 may send the pending reset signals with a plurality of different phases. The detector 602 may detect the phase information of effective edges of each pending reset signal and send the phase information to the reset signal generator 601. The reset signal generator 601 may select the optimal phase from the transmitted pending reset signal phases according to the phase information, and send the pending reset signal (i.e., the reset signal) corresponding to the optimal phase to the detector 602, which may guarantee that the one or more detectors 602 may securely reset the time counters to zero in a same cycle, thereby achieving the synchronization of the one or more detectors 602. In the case that reset channels of the one or more detectors 602 have a certain difference, the scheme of the present disclosure may ensure that the time counters of the one or more detectors 602 may be started and reset at the same time.

In some embodiments, the reset signal generator 601 may include a determination module 810. The determination module 810 may be connected to the detector 602 for determining whether the first return signal corresponds to a preset return value. In response to that the first return signal corresponds to the preset return value, the reset signal generator 601 may determine that the pending reset signal corresponding to the first return signal is the reset signal. The preset return value may be set according to a positional relationship between the pending reset signal and a same frequency clock signal corresponding to the pending reset signal. In some embodiments, the determination module 810 may receive a second return signal sent by the one or more detectors 602. The second return signal may be generated according to the reset signal by the one or more detectors 602. Further, the reset signal generator 601 may determine whether the second return signal corresponds to the preset return value. In response to that the second return signal corresponds to the preset return value, the reset signal generator 601 may send a determination instruction, that the reset signal has sent correctly, to the one or more detectors 602. The second return signal may be a binary value. In some embodiments, when the reset signal generator 601 confirms that an Nth phase has been correctly transmitted according to the second return signal, the reset signal generator 601 may send the determination instruction that the reset signal has been sent correctly. When the determination instruction is received, the time counters of the one or more detectors 602 may execute the simultaneous reset instruction. In the embodiment, the determination instruction may ensure the correctness of the reset signal received by the detector 602 and that the time counter of the detector 602 may be reset to zero and started at the same time.

Figure 9:
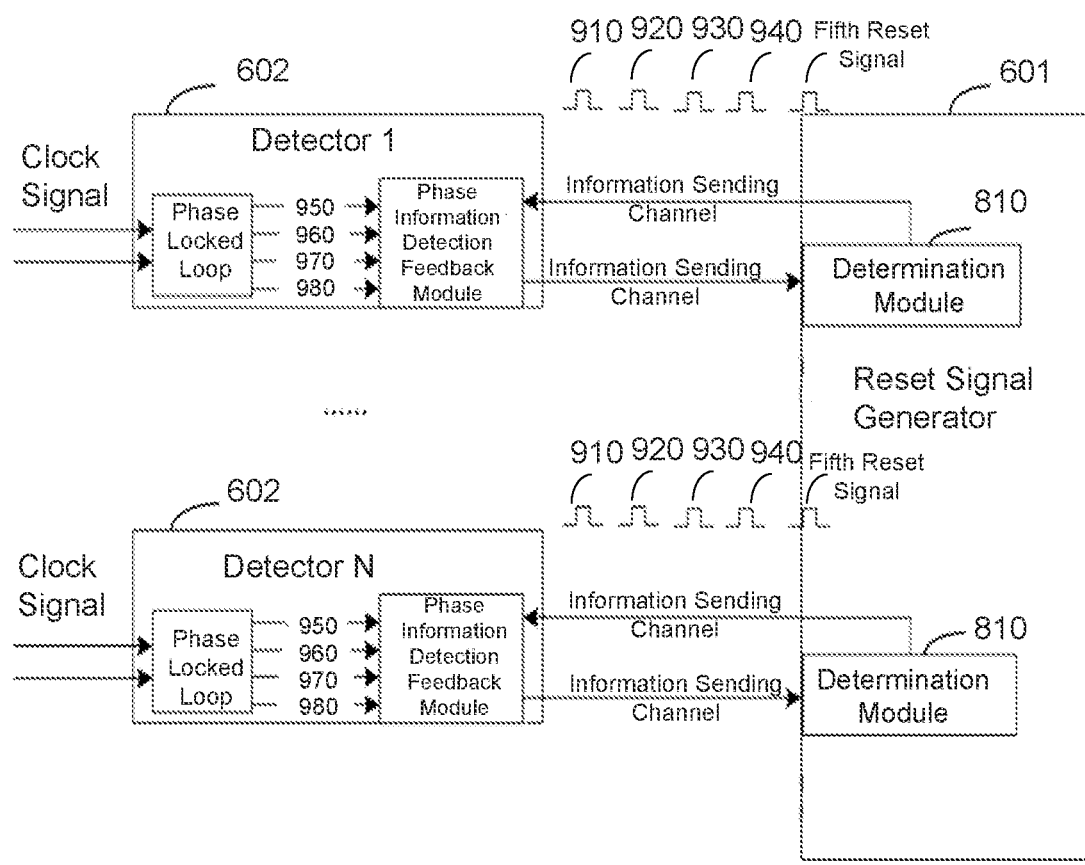
FIG. 9 is a schematic diagram illustrating an exemplary clock synchronization device according to some embodiments of the present disclosure.

FIG. 9 is a schematic diagram illustrating an exemplary clock synchronization device according to some embodiments of the present disclosure. The reset signal generator 601 may send four pending reset signals with different phases to one or more detectors 602 (e.g., detector 1, detector N), such as a pending reset signal 910 with a 0 degree phase, a pending reset signal 920 with a 90 degree phase, a pending reset signal 930 with a 180 degree phase, and a pending reset signal 940 with a 270 degree phase. The detector 602 (e.g., a phase locked loop) may generate four same frequency clock signals with different phases, such as a clock signal 950 with a 0 degree phase, a clock signal 960 with a 90 degree phase, a clock signal 970 with a 180 degree phase, and a clock signal 980 with a 270 degree phase. The detector 602 (e.g., a phase information detection feedback module) may use the four same frequency clock signals to sample each pending reset signal, respectively, obtaining a sample values and send this obtained sample values to the reset signal generator 601 through a phase information feedback channel. When the reset signal generator 601 receives a sample value 1100, it may be determined that a phase of a pending reset signal corresponding to the sample value 1100 is the optimal phase. Further, the reset signal generator 601 may designate the optimal phase as the phase of a fifth reset signal (i.e., a reset signal), and send the fifth reset signal to the detector 602. The detector 602 may reset the time counter of the detector 602 to zero according to the fifth reset signal.

FIGS. 10A-10D are schematic diagrams illustrating exemplary operations of determining a reset signal according to some embodiments of the present disclosure. FIGS. 10A-10D respectively show 4 kinds of respective positional relationships between a first pending reset signal (e.g. a pending reset signal with a phase of 0 degree) and a 0 degree clock, a 90 degree clock, a 180 degree clock, and a 270 degree clock of a detector.

Figure 10A:
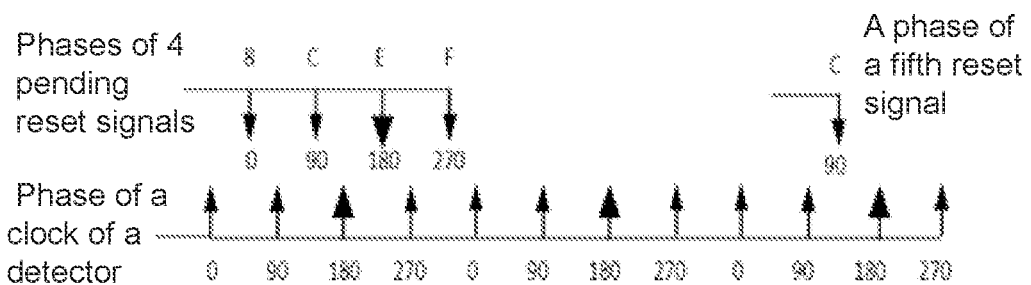
FIGS. 10A-10D are schematic diagrams illustrating exemplary operations of determining a reset signal according to some embodiments of the present disclosure.

As shown in FIG. 10A, in a first positional relationship, an effective edge (a down edge) of pending reset signal at a 0 degree phase (referred to as 0 degree pending reset signal) may be located between the 0 degree clock and the 90 degree clock of the detector 602, or on a jump edge of a clock. A first return signal captured by the detector 602 corresponding to the 0 degree pending reset signal is 1000, a first return value corresponding to the 90 degree pending reset signal is 1100, a first return value corresponding to the 180 degree pending reset signal is 1110, and a first return value corresponding to the 270 degree pending reset signal is 1111. The reset signal generator 601 may designate the phase of the pending reset signal (i.e., 90 degrees) corresponding to the first return value of 1100 as a phase of a fifth reset signal (i.e., a reset signal). The effective edge of the reset signal may locate between the 90 degree clock and the 180 degree clock, which may ensure that the 0 degree clock may stably capture the effective edge of the reset signal.

Figure 10B:
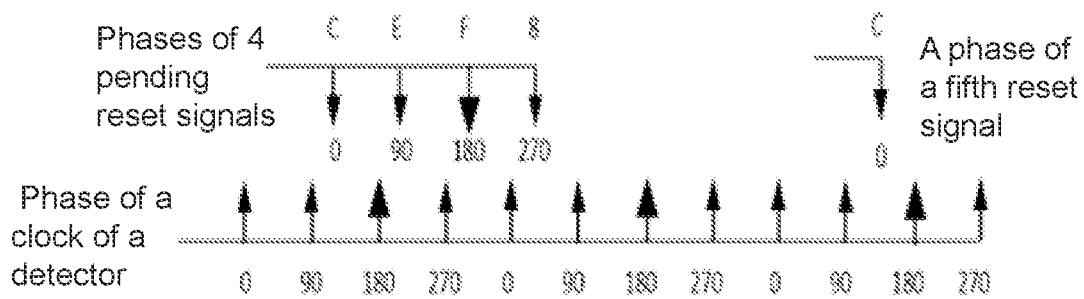

As shown in FIG. 10B, in a second positional relationship, the effective edge (the down edge) of the 0 degree pending reset signal may be located (or on the jump edge of the clock) between the 90 degree clock and the 180 degree clock of the detector 602. The first return signal captured by the detector 602 corresponding to the 0 degree pending reset signal may be 1000, the first return value corresponding to the 90 degree pending reset signal may be 1100, the first return value corresponding to the 180 degree pending reset signal may be 1110, and the first return value corresponding to the 270 degree pending reset signal may be 1111. The fifth reset signal may be designated as a 0 degree phase. The effective edge of the reset signal may locate between the 90 degree clock and the 180 degree clock, which may ensure that the 0 degree clock may stably capture the effective edge of the reset signal.

Figure 10C:
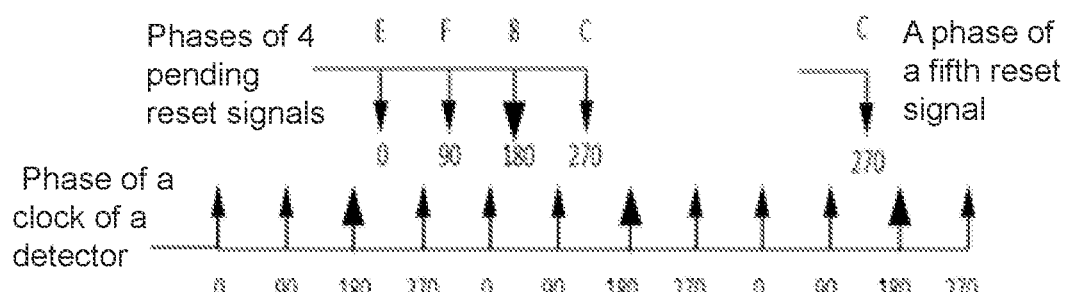
Figure 10D:
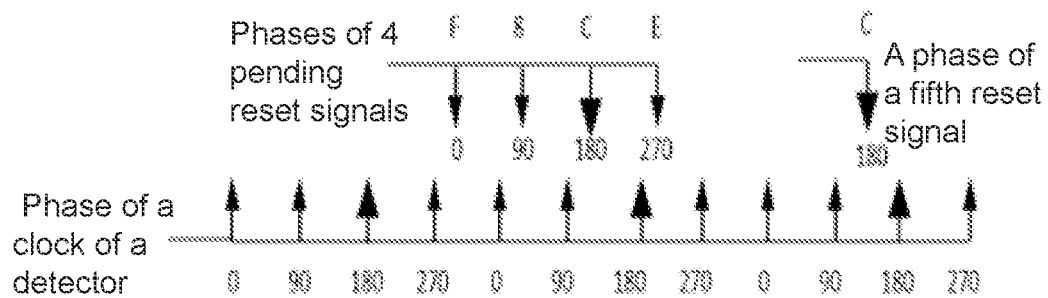

Results demonstrated in FIGS. 10C and 10D may be similarly obtained according to the discussion described above with regard to FIGS. 10A and 10B. The phase of the pending reset signal (i.e., 90 degree) corresponding to the first return value of 1100 may be designated as the phase of the fifth reset signal (i.e., the reset signal), which may ensure that the effective edge of reset signal may locate between the 90 degree clock and the 180 degree clock. Therefore, the detector 602 may use the 0 degree clock to guarantee the capture of the reset signal. When a certain difference is present in reset channels of the different detectors, for example, when the four kinds of positional relationships occur, the fifth reset signal of each channel may select the corresponding phase, which may ensure that the reset signal may be securely sampled so that all detector may reset their time counters to zero at the same time and achieve the synchronization of the different detectors.

It may be understood that the reset signal generator 601 may designate the phase of pending reset signal corresponding to the first return value of 1100 as the phase of the fifth reset signal, which may only mean that the effective edge of the reset signal is not on the jump edge, thereby avoiding sampling a jump signal. Only by way of example, when the effective edge of the reset signal is an up edge, the return value received by the reset signal generator 601 may also be other values.

In some embodiments, the present disclosure may also provide a computing device including a processor and a storage, wherein the storage stores a computer program. When executed by a processor, the computer program may direct the processor to perform a process (e.g., process 600, process 700) described elsewhere in the present disclosure.

Figure 11:
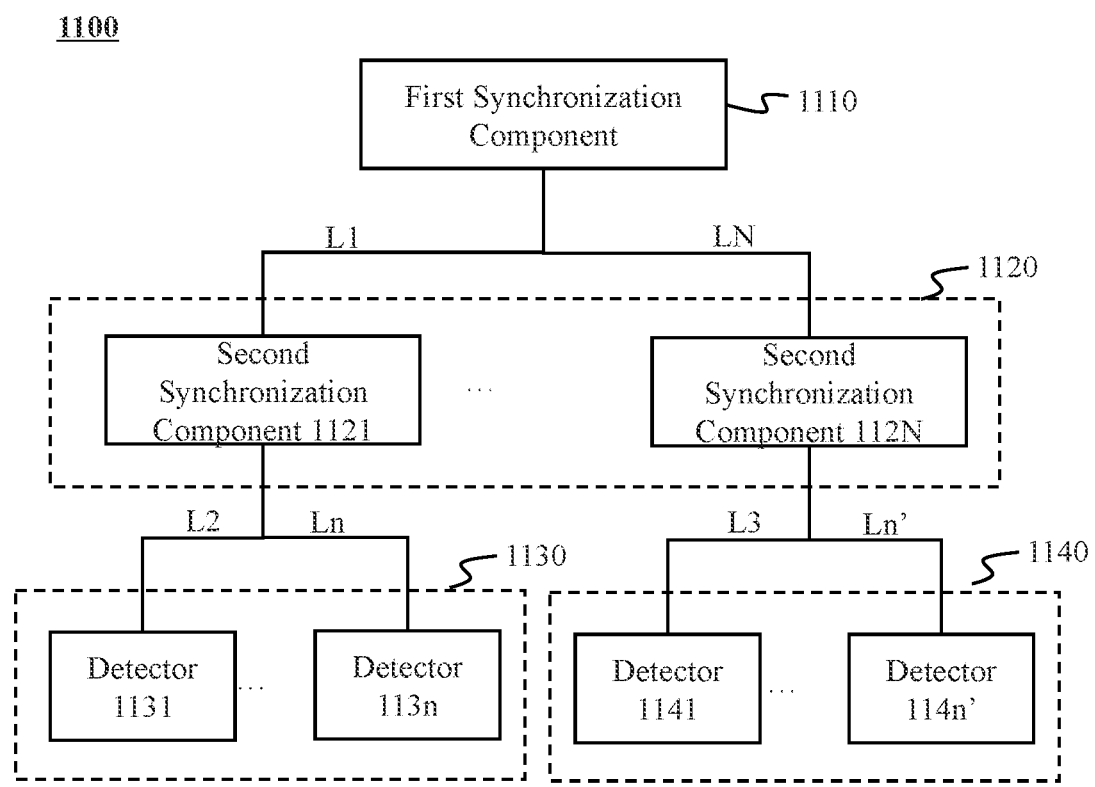
FIG. 11 is a schematic diagram illustrating an exemplary clock synchronization device according to some embodiments of the present disclosure.

FIG. 11 is a schematic diagram illustrating an exemplary clock synchronization device according to some embodiments of the present disclosure. As shown in FIG. 11, the clock synchronization device 1100 may include a first synchronization component 1110, one or more second synchronization components 1120, and one or more third synchronization components (not shown in the FIG. 11). In some embodiments, the first synchronization component 1110 and/or the second synchronization component(s) 1120 may include a digital switch circuit (DSW) with a central control and/or data switching function.

The first synchronization component 1110 may be configured to generate a first synchronization signal and transmit the first synchronization signal to the second synchronization component(s) 1120. In some embodiments, the first synchronization signal may include a digital signal, an analog signal, or any other signal. In some embodiments, the first synchronization signal may be denoted as a time varying voltage, current, electromagnetic wave, a pulse, or the like, that carries information. Preferably, the first synchronization signal may include a pulse signal. For example, the first synchronization signal may include a pulse signal with a certain frequency and/or amplitude, which may be generated by a signal generator (e.g., an oscillator crystal (OSC)) and/or processed by a signal processing unit (e.g., a signal allocation unit).

In some embodiments, the first synchronization component 1110 may include one or more signal processing units such as one or more buffer units. The buffer unit(s) may be configured to process the first synchronization signal and transmit the processed first synchronization signal to other components (e.g., the second synchronization component(s) 1120) of the clock synchronization device 1100. For example, the first synchronization component 1110 may include a first buffer unit and one or more second buffer units. The first buffer unit may be connected to the second buffer units, e.g., via a wired link, which may be configured to process the first synchronization signal and transmit the processed first synchronization signal to the second buffer unit(s). For example, the first buffer unit may generate one or more synchronization signals (e.g., one synchronization signal, two synchronization signals, four synchronization signals, etc.) based on the first synchronization signal and transmit the synchronization signal(s) to the second buffer unit(s). Each of the second buffer unit(s) may be configured to receive the first synchronization signal from the first buffer unit, and process the received first synchronization signal. After processing the first synchronization signal, a second buffer unit may transmit the first synchronization signal to the second synchronization component(s) 1120. The processing of the first synchronization signal performed by the second buffer unit may be the same as or different with the processing of the first synchronization signal performed by the first buffer unit. Merely by way of example, the second buffer unit may generate one or more first synchronization signals based on the received first synchronization signal from the first buffer unit. The number or count of each of the second buffers units may be a preset value. For example, the second buffer unit may include 1 buffer unit, 2 buffer units, 4 buffer units, n buffer units (n is a positive integer), or the like, which is not limited herein.

The buffer units (e.g., the first buffer unit, the second buffer unit(s)) disposed in the first synchronization component 1110 may process the first synchronization signal and generate one or more second synchronization signals based on the first synchronization signal, thereby increasing a count of links connecting the first synchronization component 1110 and the second synchronization component 1120, reducing a transmission load of a buffer unit, and ensuring the synchronous transmission of the first synchronization signal from the first synchronization component 1110 to the second synchronization component(s) 1120.

In some embodiments, the first synchronization component 1110 may transmit the first synchronization signal to the second synchronization component(s) 1120 via a wired link. The wired link may include a metal cable, an optical cable, a hybrid cable, a cable on a circuit board, or the like, or any combination thereof. In some embodiments, the wired link may include other units, for example, a processing unit for processing the first synchronization signal. Exemplary processing unit may include a phase locked loop (PLL), a buffer unit, or the like, or any combination thereof. In some embodiments, the first synchronization component 1110 may transmit the first synchronization signal to the second synchronization component(s) 1120 via one or more wired links (e.g., one wired link, two wired links, four wired links, etc.). The wired link may improve the transmission speed and ensure a synchronous transmission of the first synchronization signal from the first synchronization component 1110 to the second synchronization component(s) 1120.

In some embodiments, the first synchronization component 1110 may transmit the first synchronization signal to the second synchronization component(s) 1120 via equal length cables. The equal length cables may refer to a plurality of cables with an equal (or substantially equal) length or a length difference between the equal length cables is less than a length threshold (e.g., 0.01 mm, 0.1 mm, 1 mm, etc.). In some embodiments, the equal length cables may include straight equal length cables, serpentine equal-length cables, or the like, or any combination thereof. The equal length cables for transmitting the first synchronization signal may reduce an effect of other components (e.g., the components of the first synchronization component 1110 or an external source) on the transmission of the first synchronization signal, so that the transmission speed of the first synchronization signal from the first synchronization component 1110 to the second synchronization component(s) 1120 keeps constant, ensuring that the first synchronization signal is synchronously transmitted to the second synchronization component(s) 1120.

The second synchronization component(s) 1120 may include one or more second synchronization components, for example, a second synchronization component 1121, . . . , a second synchronization component 112N, wherein N refers to any positive integer greater than 1. Each of the second synchronization component(s) 1120 may receive the first synchronization signal from the first synchronization component 1110, and generate a second synchronization signal based on the first synchronization signal. In some embodiments, the second synchronization signal may be the same as or different from the first synchronization signal. For example, a number or count of the second synchronization signal may be the same as or different from that of the first synchronization signal. Specifically, the count of the second synchronization signal may be 2, 4, 8, 12, etc., and a count of the first synchronization signal may be 1. As another example, a type of the second synchronization signal may be the same as or different from that of the first synchronization signal. Specifically, the type of the first synchronization signal may be a digital signal, and the type of the second synchronization signal may be a digital signal or an analog signal. In some embodiments, the second synchronization component(s) 1120 may perform a processing operation on the first synchronization signal to generate the second synchronization signal. Exemplary processing operation performed by the second synchronization component(s) 1120 may include a frequency adjustment operation, a filtering operation, a denoising operation, an enhancement operation, a smoothing operation, a transformation operation, or the like, or a combination thereof.

In some embodiments, the second synchronization component(s) 1120 may transmit the second synchronization signal to the third synchronization component(s) via the wired link, which may improve a transmission speed and ensure a synchronous transmission of the second synchronization signal from each of the second synchronization component 1120 to the third synchronization component(s).

In some embodiments, the second synchronization component(s) 1120 may include one or more signal processing units such as one or more buffer units. For example, the second synchronization component(s) may include a third buffer unit and one or more fourth buffer units. The third buffer unit may be configured to transmit the second synchronization signal to the one or more fourth buffer units. Each of the one or more fourth buffer units may be configured to transmit the second synchronization signal to the third synchronization component(s). The buffer unit(s) of the second synchronization component(s) 1120 may be the same as or similar to that of the first synchronization component 1110, which are not repeated herein.

In some embodiments, the third synchronization component(s) may be disposed in a detector to reset a clock of the detector. As shown in FIG. 11, the third synchronization component(s) may be correspondingly disposed in a detector 1131, . . . , and a detector 113n, and a detector 1141, . . . , and a detector 114n', wherein n and/or n' refer to any positive integer greater than 1 . . . . In some embodiments, one or more detectors may compose of a detector set. For example, the detector 1131, . . . , and the detector 113n may compose of a detector set 1130. As another example, the detector 1141, . . . , and the detector 114n' may be composed of a detector set 1140. The detectors of the one or more detector sets may be configured to synchronously detect radiation photons emitted from a same portion or different portions of a target subject. For example, the detector set 1130 may be configured to detect radiation photons emitted from the head of the subject, and the detector set 1140 may be configured to detect radiation photons emitted from a leg of the subject. A PET imaging system (e.g., the imaging system 100) may construct an image associated with the subject based on data acquired by the one or more detector sets.

In some embodiments, the second synchronization component(s) 1120 may transmit the second synchronization signal to the one or more detectors of the detector set(s) via wired link(s). For example, the second synchronization component 1121 may synchronously transmit the second synchronization signal to the detector 1131, . . . , and the detector 113n of the detector set 1130 via a wired link L2, . . . , Ln, respectively. As another example, the second synchronization component 112N may synchronously transmit the second synchronization signal to the detector 1141, . . . , and the detector 114n' of the detector set 1140 via a wired link L3, . . . , Ln', respectively. One or more detectors of one detector unit may synchronously receive the second synchronization signal, thereby realizing a clock synchronization or a reset synchronization of the detector(s). In some embodiments, a number or count of the detector sets or the detectors of each of the detector sets may be predetermined by the processing device 140. For example, the count of the detector sets may be determined as 2, 4, 6, 8, etc. Alternatively, the count of the detector sets or the detectors of each of the detector sets may be determined based on actual needs (e.g., a scanning protocol).

In some embodiments, the first synchronization signal and/or the second synchronization signal may include a synchronization clock signal and/or a synchronization reset signal. The synchronization clock signal may refer to a signal which may oscillate between a high and a low state, which may be configured to coordinate actions of a device to be synchronous. The synchronization reset signal may refer to a signal which may be used to clear a pending error or event of the component(s) of the device (e.g., the clock synchronization device 1100 and/or the component(s) of the clock synchronization device 1100) to reset the detectors to an initial state.

In some embodiments, a transmission time for transmitting the first synchronization signal from the first synchronization component 1110 to each of the one or more second synchronization component(s) 1120 may be the same. As shown in FIG. 11, a transmission time for transmitting the first synchronization signal from the first synchronization component 1110 to the second synchronization component 1121 via the link L1 may be the same as a transmission time for transmitting the first synchronization signal from the first synchronization component 1110 to the second synchronization component 112N via the link LN. In some embodiments, a transmission time for transmitting the second synchronization signal from each of the one or more second synchronization components to each of the one or more third synchronization components may be the same. For example, a transmission time for transmitting the second synchronization signal from the second synchronization component 1121 to the detector 1131 via the link L2 may be the same as a transmission time for transmitting the second synchronization signal from the second synchronization component 112N to the detector 114n' via the link Ln'.

The same transmission time of a synchronization signal (e.g., the first synchronization signal, the second synchronization signal, etc.) may allow a signal skew of the synchronization signal less than a skew threshold. The signal skew refers to a time difference between or among time points at which a synchronization signal is received by different components of the clock synchronization device 1100. For example, a signal skew may include a time difference between the time point that the second synchronization component 1121 receives the first synchronization signal and the time point that the second synchronization component 112N receives the first synchronization signal. In some embodiments, the skew threshold may be determined by the imaging system. For example, the imaging system 100 may determine that the skew threshold in a picosecond (ps) level, for example, 0.05 ps, 0.1 ps, 1 ps, etc. As another example, the imaging system 100 may determine that the same transmission time of a synchronization signal may less than a time threshold (e.g., ¼ of a clock cycle, ⅓ of a clock cycle, etc.). Alternatively, the skew threshold may be determined based on actual needs.

In some embodiments, the transmission time for transmitting the first synchronization signal from the first synchronization component to each of the one or more second synchronization components and/or the transmission time for transmitting the second synchronization signal from each of the one or more second synchronization components to each of the one or more third synchronization components may be determined by controlling the count of the links, the length of the links, the type of the links. For example, a component may be disposed on a link connecting a first synchronization component A and a second synchronization component B, which may cause a transmission decay of the first synchronization signal. The length of the link connecting the first synchronization component A and the second synchronization component B may be adjusted (e.g., shorten or lengthen) to ensure that the transmission time of the first synchronization signal transmitted from the first synchronization component A and second synchronization component B may be same (or substantially same) as the transmission time for transmitting the first synchronization signal from the first synchronization component A to other second synchronization components. As another example, the first synchronization signal may be transmitted to each of the second synchronization component(s) 1120 via a differential transmission link, which may effectively control a transmission speed of the first synchronization signal, ensuring that each of the second synchronization component(s) 1120 may synchronously receive the first synchronization signal, and improve anti-interference performance of the transmission link. In some embodiments, the transmission time for transmitting the first synchronization signal from the first synchronization component 1110 to each of the second synchronization component(s) 1120 may be adjusted and/or controlled by a controller, for example, a PLL. The first synchronization component 1110 may transmit the first synchronization signal to the PLL. The PLL may be configured to adjust a frequency, a phase, or the like, of the first synchronization signal and transmit the adjusted first synchronization signal to the second synchronization component(s) 1120.

In some embodiments, the transmission time for transmitting the second synchronization signal from each of the second synchronization component(s) to each of the third synchronization components may be controlled and/or adjusted according to above mentioned manners, which may be not repeated herein. The detectors of the clock synchronization device 1100 may synchronously receive the second synchronization signal at a same (or substantially same) time, thereby effectively to synchronize or reset the detectors.

The first synchronization component 1110 may be connected to the second synchronization component(s) 1120 via equal-length cables. The first synchronization component 1110 may be configured to generate a synchronization signal, and synchronously transmit the synchronization signal to the second synchronization component(s) 1120. The synchronization signal may include a synchronization clock signal, a synchronization reset signal, or the like, or any combination thereof. After generating the synchronization signal, the first synchronization component 1110 may transmit the first synchronization signal to the second synchronization component(s) 1120. The second synchronization component(s) 1120 may receive the synchronization signal at the same time.

The second synchronization component(s) 1120 may be connected to one or more detectors via equal-length cables. The second synchronization component(s) 1120 may be configured to receive the synchronization signal and transmit the synchronization signal to the detector(s). In some embodiments, the equal-length cables may connect the first synchronization component 1110 and the second synchronization component(s) 1120, the second synchronization component(s) 1120 and the detector(s) via a quick latch connector (QLA), or any other connector. The equal-length cables may be used to ensure that the synchronization signal may be synchronously transmitted from the first synchronization component 1110 to the second synchronization component(s) 1120 and/or from the second synchronization component(s) 1120 to the detector(s). Therefore, the detectors may synchronously receive the synchronization signal generated by the first synchronization component 1110. The length of the equal-length cables may be determined according to different conditions, for example, the length of the equal length cables may be determined as 2.3 m, which may be not limited in the present disclosure.

After the detector(s) synchronously received the synchronization signal, scanning data associated with the subject may be synchronously collected. After the detectors synchronously receive the synchronization reset signal, a counter within each of the detectors may be reset to zero at the same time, thereby synchronizing states of the detector(s) in the PET system.

It should be noted that the example in FIG. 11 and the description thereof is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, the connections between components of the first synchronization component 1110 in FIG. 11 are illustrative. Any two components of the clock synchronization device 1100 may be connected or not. The connection between two components of the clock synchronization device 1100 may be a one-way connection or two-way connection. In some embodiments, the clock synchronization device 1100 may include one or more additional components or one or more components described above may be omitted.

Figure 12:
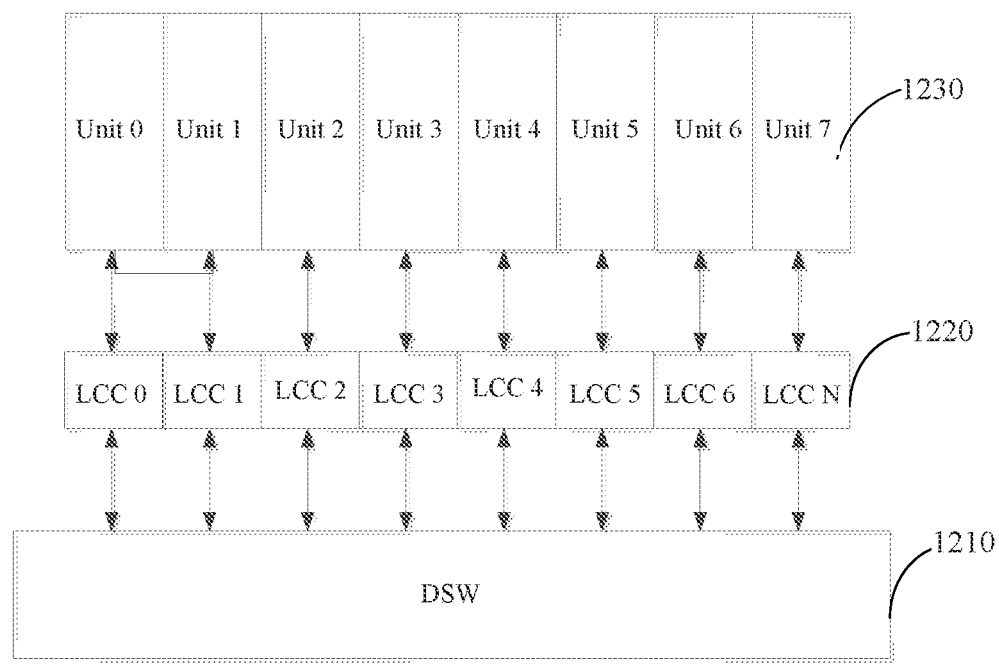
FIG. 12 is a schematic diagram illustrating an exemplary clock synchronization device according to some embodiments of the present disclosure.

FIG. 12 is a schematic diagram illustrating an exemplary clock synchronization device according to some embodiments of the present disclosure. The clock synchronization device 1200 may be an exemplary embodiment of the clock synchronization device 1100 as described in connection with FIG. 11. As shown in FIG. 12, the clock synchronization device 1200 may include a first synchronization component 1210, a second synchronization component 1220, and one or more detector sets 1230.

As shown in FIG. 12, the first synchronization component 1210 may include a DSW with a central control and/or data switching function. The second synchronization component 1220 may include one or more logical coincidence circuits (LCCs) with a distributed local function and/or a cross-composite computing function. The LCCs may include a LCC0, a LCC1, a LCC2, . . . , a LCCN. The LCCs may be connected to the DSW via equal-length cables. The LCCs may be connected to the one or more detector sets 1230 via the equal-length cables. The one or more detector sets 1230 may be denoted as Unit 0, Unit 1, . . . , Unit N. Each of the one or more detector sets 1230 may include one or more detectors. The DSW may be configured to generate a synchronization signal, process the synchronization signal to obtain a plurality of synchronization signals, and correspondingly transmit the plurality of synchronization signals to a LCC. Each of the LCCs may further process the received synchronization signal to obtain a plurality of synchronization signals and transmit the plurality of synchronization signals to the detector(s) 130. It should be noted that the DSW and the LCC may be taken as examples to illustrate the clock synchronization device 1200 in the following descriptions.

The clock synchronization device 1200 may include a first synchronization component 1210 and one or more second synchronization components 1220, which may be cascaded. The first synchronization component 1210 may be connected to the second synchronization component(s) 1220 via equal-length cables. The second synchronization component 1220 may be correspondingly connected to the one or more detectors via the equal-length cables. The first synchronization component 1110 may generate the first synchronization signal and transmit it to the one or more second synchronization components 1220. The synchronization signal may include a synchronization clock signal and/or a synchronization reset signal. The one or more second synchronization components 1220 may receive the synchronization signal and synchronously transmit the synchronization signal to the detectors. Each of the detectors may synchronously receive a same synchronization clock signal and/or a synchronization reset signal and execute thereof. Therefore, a problem such as a clock synchronization offset, an asynchronous reset, or the like, or any combination thereof, may be solved.

Figure 13:
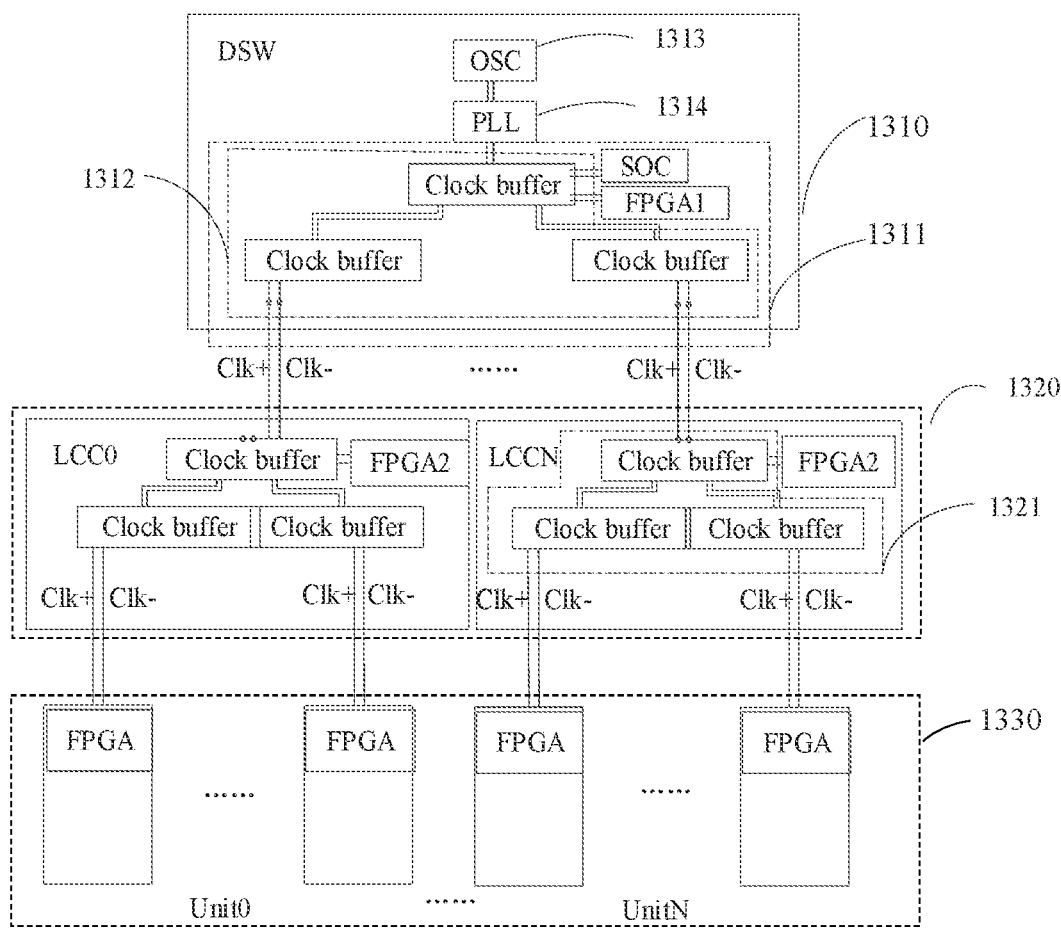
FIG. 13 is a schematic diagram illustrating an exemplary clock synchronization device according to some embodiments of the present disclosure.

FIG. 13 is a schematic diagram illustrating an exemplary clock synchronization device according to some embodiments of the present disclosure. The clock synchronization device 1300 may be an exemplary embodiment of the clock synchronization device 1100 as described in connection with FIG. 11. As shown in FIG. 13, the first synchronization component 1310 may further include a clock generation unit and a first allocation unit 1311. The clock generation unit may include an OSC 1313. The OSC 1313 may be taken as an example clock generation unit to illustrate the clock synchronization device 1300 in the following descriptions.

The OSC 1313 may be connected to the first allocation unit 1311. The OSC 1313 may be configured to generate a clock signal and send the clock signal to the first allocation unit 1311. The first allocation unit 1311 may be connected to a plurality of second synchronization components 1320. The first allocation unit 1311 may be configured to receive the clock signal, generate a synchronization clock signal, and synchronously transmit the synchronization clock signal to the plurality of second synchronization components 1320.

The OSC 1313 may generate the clock signal with a stable frequency and/or amplitude, and send the generated clock signal to the first allocation unit 1311. The first allocation unit 111 may receive and allocate the clock signal.

In some embodiment, the first allocation unit 1311 may include a first allocation subunit 1312, a reset signal generation subunit, and a reset signal allocation subunit. The first allocation subunit 1312 may be connected to the reset signal generation subunit, the reset signal allocation subunit, and the plurality of second synchronization components 1320, respectively. The first allocation subunit 1312 may receive the clock signal, generate a synchronization clock signal based on the clock signal, and synchronously transmit the synchronization clock signal to a system on chip (SOC), a first field programmable gate array (FPGA1), and the plurality of second synchronization components 1320. In this embodiment, the SOC may be taken as the reset signal generation subunit, a field programmable gate array (FPGA) may be taken as the reset signal generation subunit to describe the embodiment. The first allocation subunit 1312 may synchronously transmit the synchronization clock signal to the SOC and the FPGA in the DSW, thereby that ensuring the clock synchronization device 1300 of a PET system may transmit and receive a reset pulse. A signal sending end and a signal receiving end of the FPGA may be driven by one synchronization clock signal, which may stably, accurately, and synchronously synchronize and/or reset one or more detectors 1330.

In some embodiments, the first allocation subunit 1312 may include one or more clock buffer(s). The clock buffer(s) may be configured to generate a plurality of synchronization signals which may be independent with each other. The clock buffer may be taken as a clock allocation circuit to illustrate the embodiment. Each of the clock buffer(s) may include one or more pins. One of the pins may be connected to the OSC for receiving the clock signal generated by the OSC, and the remaining pins of the clock buffer may be correspondingly connected to the second synchronization components 1320, for example, via equal-length cables, for performing a differential processing operation on the received clock signal to generate a plurality of synchronization clock signals, and synchronously transmitting the plurality of synchronization clock signals to the plurality of second synchronization components 1320. The plurality of second synchronization components 1320 may synchronously receive a same synchronization clock signal which may be generated by a same source at a same time.

In some embodiments, the first allocation subunit 1312 may include a cascaded multi-level clock allocation circuit. As shown in FIG. 3, the first allocation subunit 1312 may include a cascaded two-level clock allocation circuit, for example, a cascaded two-level clock buffer. The cascaded two-level clock buffer may include a first level clock buffer and two second level clock buffers. One end of the first clock buffer may be connected to the OSC, and the other end of the first level clock buffer may be connected to the two second clock buffers, the SOC, and the FPGA1, respectively. After receives the clock signal, the first level clock buffer may generate two synchronization clock signals which may be independent with each other. The first level clock buffer may transmit the two synchronization clock signals to the second synchronization components 1320. The synchronization clock signal may be transmitted to the second synchronization components 1320 via the cascaded two-level clock buffer, which may improve the load carrying capacity of the OSC, reduce the interference and impact of the load on the OSC, and improve transmission stability of the synchronization clock signal.

In some embodiment, a channel skew of the first level clock buffer may be below a ps level, and a clock jitter of the first level clock buffer may be at an fs level. Since the clock signal may be used to determine a flight time of photons from the detector(s) 1330. A period for determining the flight time may include a period from a time point that the detector(s) 1330 receives the photons to a time point that a rising edge of a next clock cycle occurs. The rising edges received by different detectors of the detectors 1330 may be aligned, that is, the less the skew between the channels, the better. The channel skew of the first level clock buffer which may be below the ps level may improve the determination accuracy of the flight time of the photons, thereby improving the time resolution of the clock synchronization device 1300.

In some embodiment, the first synchronization component 1310 may include a PLL. The PLL may be connected to the OSC 1313 and the first allocation unit 1311, respectively, and configured to receive the clock signal. The PLL may control a frequency of the clock signal and send the clock signal to the first allocation unit 1311. In some embodiments, the PLL may be with a high accuracy, and a clock jitter of the PLL may be at the fs level. After receives the clock signal, the PLL may transmit the clock signal to the first level clock buffer via a differential transmission mode.

A rough time counter of each of the detector(s) 1330 may count the time after being powered on. A synchronization reset signal may be used to synchronize the rough time counter of each of the detector(s) 1330. A data cache space of the first synchronization component 1310 and/or the second synchronization components 1320 may be cleared. Therefore, it is desirable to provide the clock synchronization device 1300 to perform the above mentioned functions. When the PET system is powered on or before that the PET system starts to sanc a target subject, the first synchronization component 1310 may transmit a synchronization reset instruction to a reset signal allocation subunit using the reset signal generation subunit. The reset signal generation subunit may convert the synchronization reset instruction into a reset pulse in a clock domain. The reset pulse may be transmitted to the clock allocation circuit via a differential transmission mode. The clock allocation circuit may transmit the reset pulse to the second synchronization components 1320 via equal-length cables.

As shown in FIG. 13, the second synchronization components 1320 may include a second reset signal allocation subunit. The second reset signal allocation subunit may be connected to first synchronization component 1310, receive the synchronization signal, and transmit a plurality of synchronization signals to the detector(s) 1330. The second reset signal allocation subunit may include a second field programmable gate array chip (FPGA2) and a second allocation subunit 1321. The second allocation subunit 1321 may be configured to allocate and/or transmit the synchronization signal. In some embodiments, the second allocation subunit 1321 may include a multi-level clock allocation circuit.

As shown in FIG. 13, the multi-level clock allocation circuit may include a multi-level clock buffer. One end of the clock allocation circuit may be connected to the first synchronization component 1310, and the other end of the clock allocation circuit may be connected to the FPGA2 and detector(s) 1330. The clock allocation circuit may be configured to receive the synchronization signal and transmit the synchronization signal to the FPGA2 and the detector(s) 1330.

Figure 14:
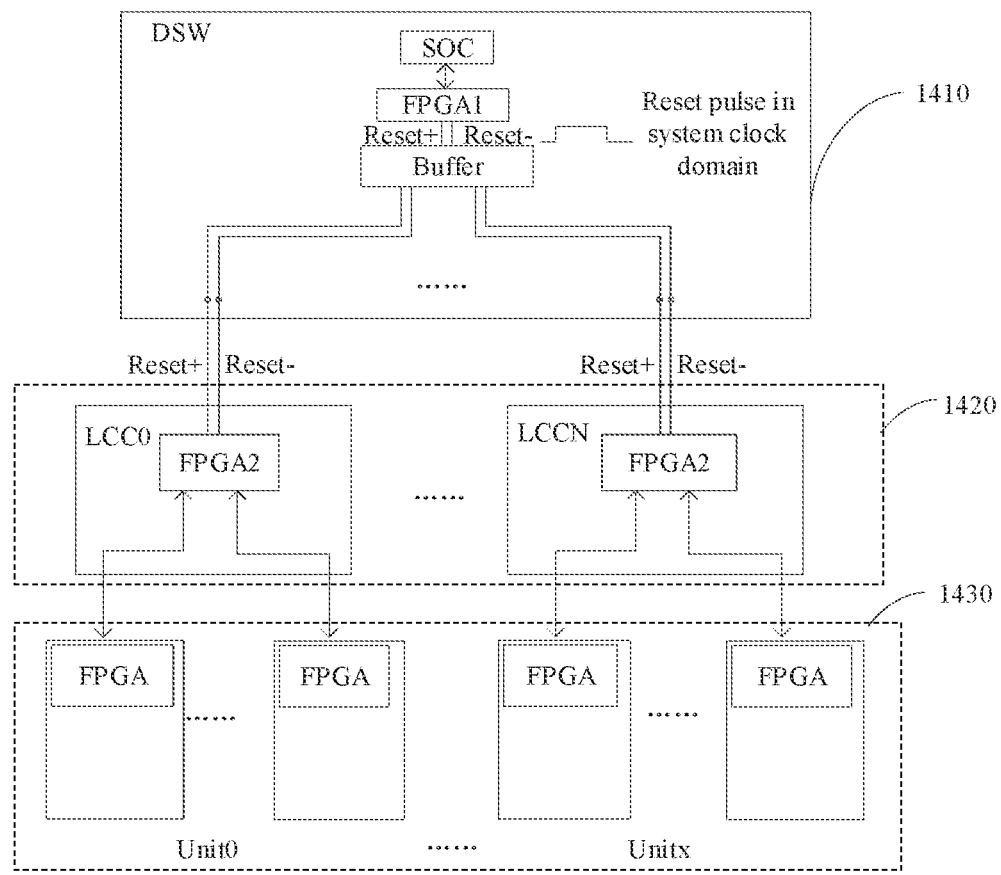
FIG. 14 is a schematic diagram illustrating an exemplary clock synchronization device according to some embodiments of the present disclosure.

FIG. 14 is a schematic diagram illustrating an exemplary clock synchronization device according to some embodiments of the present disclosure. The clock synchronization device 1400 may be an exemplary embodiment of the clock synchronization device 1100 as described in connection with FIG. 11.

As shown in FIG. 14, a second allocation subunit may be integrated in a second reset signal allocation subunit. A reset signal generation subunit may be connected to a first reset signal allocation subunit and configured to transmit a synchronization reset instruction to the first reset signal allocation subunit. The reset signal generation subunit may be configured to generate a synchronization reset signal and transmit the synchronization reset signal to a first allocation subunit. The first allocation unit may be configured to receive the synchronization reset signal and synchronously transmit the synchronization reset signal to a plurality of second synchronization components 1420.

The second synchronization components 1420 may transmit the synchronization reset signal to one or more detectors 1430 using the second reset signal allocation subunit. Specifically, the second reset signal allocation subunit may include the FPGA2. The FPGA2 may be connected to first synchronization component 1410. The FPGA2 may be configured to receive the synchronization reset signal and transmit the synchronization reset signal to the detector(s) 1430, that is, the FPGA2 may be configured to allocate and/or transmit the synchronization reset signal. As shown in FIG. 14, the first reset signal allocation subunit may include the FPGA1, and the first allocation subunit may include a buffer.

In some embodiments, the FPGA2 may be configured to allocate the synchronization reset signal, that is, after receives the synchronization reset signal, the FPGA2 may transform the synchronization reset signal into one or more synchronization reset signals. The FPGA2 may correspondingly transmit the one or more synchronization reset signals to the detector(s) 1430. It can be understood that, the second synchronization component(s) 1420 may include a clock allocation circuit which may be configured to allocate the synchronization reset signal.

Specifically, when the second synchronization component(s) 1420 (e.g., the LCC) receive a differential reset pulse, data buffer space and status of the LCC may be cleared and a reset pulse may be generated and allocated to an FPGA of each of the detector(s) 1430 in a detector set. The reset pulse may be transmitted via equal-length cables. After the FPGA of a detector receives the reset pulse, a rough time counter and/or data cache of the detector may be cleared. Since one or more detectors 1430 of the PET system may synchronously receive the reset pulse, the FPGA of each of the detector(s) 1430 may correspondingly clear a rough time counter and/or data cache of a detector, thereby synchronously resetting the detector(s) 1430.

Figure 15:
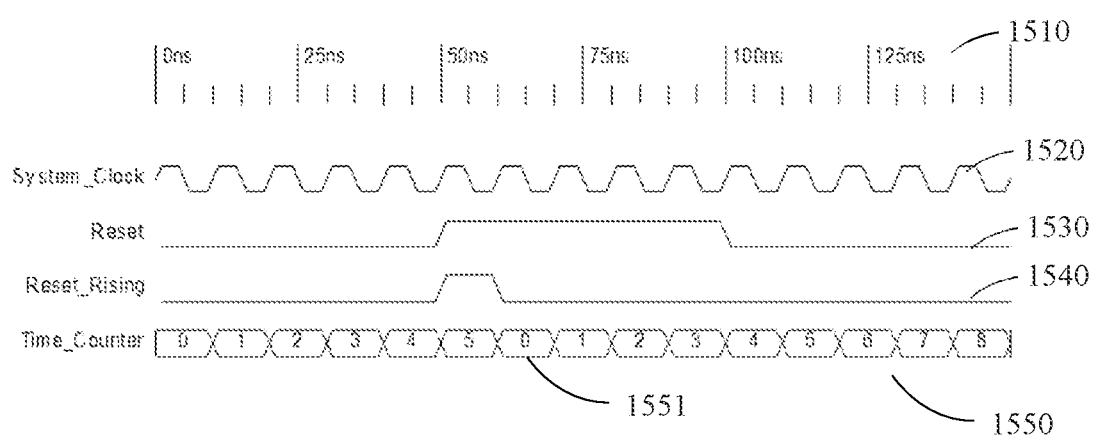
FIG. 15 is a schematic diagram illustrating an exemplary rough time counter of a detector according to some embodiments of the present disclosure.

FIG. 15 is a schematic diagram illustrating an exemplary rough time counter of a detector according to some embodiments of the present disclosure.

As shown in FIG. 15, a counting and/or a resetting mode of a rough time counter of each of one or more detectors may be described in the following.

A timeshaft 1510 may present a working time of a clock synchronization device. A synchronization clock signal, a synchronization reset signal received by a FPGA of a detector may be represented by System_Clock 1520, Reset 1530, respectively. The rough time counter may refer to a component which may be configured to store and/or display a number of times of an event or process has occurred in relationship to a clock, which may be represented by a Time_Counter 1550 as shown in FIG. 15. The System_Clock 1520 and the Reset 1530 may be obtained from a clock synchronization device (e.g., the clock synchronization device 1100, 1200, 1300, 1400, etc.). When the clock synchronization device detects that a Reset_Rising 1540 occurs in the Reset 1530, the Time_Counter 1550 may be reset to zero as represented by a point 1551.

When a PET system is powered on or starts to collect data, the Time_Counters of one or more detectors may be synchronously reset to zero after a SOC of a DSW sends a synchronization reset instruction. Time baselines of the detectors may be aligned. Subsequently, an LCC may complete the synchronization of clock counting based on a value of the Time_Counter 1550, a time to digital converter (TDC), and window width information.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction performing system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for clock synchronization, comprising:
   a reset signal generator connected with a plurality of detectors, wherein the reset signal generator is configured to:
      generate a set of preliminary reset signals, each of which has a different phase, to be detected; and
      transmit the set of preliminary reset signals to the plurality of detectors;
   wherein each of the plurality of detectors is configured to:
      generate first feedback data for each of the set of preliminary reset signals; and
      transmit the first feedback data to the reset signal generator;
   wherein the reset signal generator is further configured to:
      for each of the plurality of detectors, generate a reset signal based on the first feedback data; and
      transmit the reset signal to each of the plurality of detectors;
   wherein each of the plurality of detectors is further configured to:
      execute a clock synchronization in itself based on the reset signal.

2. The system of claim 1, wherein to generate the first feedback data for each of the set of preliminary reset signals, each of the plurality of detectors is further configured to:
   for each of the set of preliminary reset signals, correspondingly generate a sequence of sampling values based on a sequence of clock cycle iteration with different phases; and
   take the sequence of sampling values as the first feedback data.

3. The system of claim 2, wherein to generate the reset signal based on the first feedback data, the reset signal generator is further configured to:
   determine an optimum phase of the reset signal, wherein a sampling value of a preliminary reset signal, of the plurality of the preliminary reset signal, with the optimum phase is positive, the sampling value is predicted based on the clock cycle iteration with a zero phase; and
   generate the reset signal with the optimum phase.

4. The system of claim 2, wherein to generate the reset signal based on the first feedback data, the reset signal generator is further configured to:
   determine an optimum preliminary reset signal, of which a first value of the sequence of sampling values is positive; and
   generate the reset signal with the phase of the optimum preliminary reset signal.

5. The system of claim 1, wherein:
   each of the plurality of detectors is further configured to:
      generate second feedback data based on the reset signal; and
      transmit the second feedback data to the reset signal generator;
   the reset signal generator is further configured to:
      determine whether the second feedback data corresponds to a predetermined value; and
      in response to determining that the second feedback data corresponds to the predetermined value, transmit a determination instruction indicating that the reset signal has been correctly transmitted.

6. The system of claim 1, wherein to generate the first feedback data for each of the set of preliminary reset signals, each of the plurality detectors is further configured to:
   perform detection based on a frequency higher than a standard clock frequency;
   obtain a time difference between the preliminary reset signal and the standard clock cycle; and
   designate the time difference as the first feedback data.

7. The system of claim 2, wherein for generate a sequence of sampling values based on a sequence of clock cycle iteration with different phases, each of the plurality detectors is further configured to:
   generate a plurality of clock signals with different phases; and
   sample a preliminary reset signal based on the plurality of clock signals to generate the sequence of sampling values of the preliminary reset signal.

8. The system of claim 3, wherein to determine an optimum phase of the reset signal, the reset signal generator is further configured to:
   determine phases of the plurality of preliminary reset signals; and
   determine the optimum phase of the reset signal based on the phases of the plurality of preliminary reset signals.

9. The system of claim 8, wherein to determine phases of the plurality of preliminary reset signals, the reset signal generator is further configured to:
   determine the phase of one of the plurality of preliminary reset signals based on a relationship between a pulse signal of the preliminary reset signal and a clock cycle.

10. The system of claim 2, wherein to generate the reset signal based on the first feedback data, the reset signal generator is further configured to:
    select a preliminary reset signal corresponding to a minimum time difference from the set of preliminary reset signals as the reset signal.

11. A method for clock synchronization, comprising:
    generating, by a reset signal generator connected with a plurality of detectors, a set of preliminary reset signals, each of which has a different phase, to be detected;
    transmitting the set of preliminary reset signals by the reset signal generator to the plurality of detectors;
    for each of the set of preliminary reset signals, generating first feedback data by each of the plurality of detectors;
    transmitting the first feedback data by each of the plurality of detectors to the reset signal generator;
    for each of the plurality of detectors, generating a reset signal by the reset signal generator based on the first feedback data;

transmitting the reset signal by the reset signal generator to each of the plurality of detectors; and executing a clock synchronization in each of the plurality detectors based on the reset signal.

12. The method of claim 11, wherein for each of the set of preliminary reset signals, the generating first feedback data by each of the plurality of detectors includes:

for each of the set of preliminary reset signals, correspondingly generating a sequence of sampling values based on a sequence of clock cycle iteration with different phases; and taking the sequence of sampling values as the first feedback data.

13. The method of claim 12, wherein for each of the plurality of detectors, the generating a reset signal by the reset signal generator based on the first feedback data includes:

determining an optimum phase of the reset signal, wherein a sampling value of a preliminary reset signal, of the plurality of the preliminary reset signal, with the optimum phase is positive, the sampling value is predicted based on the clock cycle iteration with a zero phase; and generating the reset signal with the optimum phase.

14. The method of claim 12, wherein for each of the plurality of detectors, the generating a reset signal by the reset signal generator based on the first feedback data includes:

determining an optimum preliminary reset signal, of which a first value of the sequence of sampling values is positive; and generating the reset signal with the phase of the optimum preliminary reset signal.

15. The method of claim 11, wherein:

generating second feedback data by each of the plurality of detectors based on the reset signal;

transmitting the second feedback data by each of the plurality of detectors to the reset signal generator;

determining, by the reset signal generator, whether the second feedback data corresponds to a predetermined value; and in response to determining that the second feedback data corresponds to the predetermined value, transmitting, by the reset signal generator, a determination instruction indicating that the reset signal has been correctly transmitted.

16. The method of claim 12, wherein for each of the plurality of detectors, the generating a reset signal by the reset signal generator based on the first feedback data further includes:

generating a plurality of clock signals with different phases; and sampling a preliminary reset signal based on the plurality of clock signals to generate the sequence of sampling values of the preliminary reset signal.

17. The method of claim 12, wherein for each of the plurality of detectors, the generating a reset signal by the reset signal generator based on the first feedback data includes:

selecting a preliminary reset signal corresponding to a minimum time difference from the set of preliminary reset signals as the reset signal.

18. The method of claim 12, wherein for each of the plurality of detectors, the generating a reset signal by the reset signal generator based on the first feedback data further includes:

performing detection based on a frequency higher than a standard clock frequency;

obtainning a time difference between the preliminary reset signal and the standard clock cycle; and designating the time difference as the first feedback data.

19. The method of claim 12, wherein for each of the plurality of detectors, the generating a reset signal by the reset signal generator based on the first feedback data further includes:

determining phases of the plurality of preliminary reset signals; and determining the optimum phase of the reset signal based on the phases of the plurality of preliminary reset signals.

* * * * *